United States Patent
Armitstead et al.

(10) Patent No.: US 12,064,255 B2
(45) Date of Patent: *Aug. 20, 2024

(54) RESPIRATORY PRESSURE THERAPY SYSTEM

(71) Applicant: ResMed Inc., San Diego, CA (US)

(72) Inventors: Jeffrey Peter Armitstead, Sydney (AU); Mark David Buckley, Sydney (AU); Michael Waclaw Colefax, Sydney (AU); Susan Robyn Lynch, Maitland (AU); Dion Charles Chewe Martin, Sydney (AU); Gregory Robert Peake, Petersham (AU); Dinesh Ramanan, Sydney (AU); Jamie Graeme Wehbeh, Sydney (AU); Natalie Zotelo, Sydney (AU)

(73) Assignee: ResMed Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/672,808

(22) Filed: Feb. 16, 2022

(65) Prior Publication Data

US 2022/0257180 A1  Aug. 18, 2022

Related U.S. Application Data

(63) Continuation of application No. 15/520,663, filed as application No. PCT/AU2015/050655 on Oct. 23, 2015, now Pat. No. 11,278,239.

(Continued)

(51) Int. Cl.
*A61B 5/00* (2006.01)
*A61B 5/08* (2006.01)
(Continued)

(52) U.S. Cl.
CPC .......... *A61B 5/4833* (2013.01); *A61B 5/0004* (2013.01); *A61B 5/0022* (2013.01);
(Continued)

(58) Field of Classification Search
CPC .............. A61M 16/00; A61M 16/0021; A61M 16/0022; A61M 16/0051; A61M 16/0069;
(Continued)

(56) References Cited

U.S. PATENT DOCUMENTS 4,944,310 A   7/1990  Sullivan
5,517,983 A   5/1996  Deighan et al.
(Continued)

FOREIGN PATENT DOCUMENTS

CN   101500633 A   8/2009
CN   101912266 A   12/2010
(Continued)

OTHER PUBLICATIONS

Chinese Office Action issued in corresponding Chinese application No. 201580069094 on Jan. 30, 2019.
(Continued)

*Primary Examiner* — Justine R Yu
*Assistant Examiner* — Matthew D Ziegler
(74) *Attorney, Agent, or Firm* — Botos Churchill IP Law LLP

(57) ABSTRACT

Apparatus and methods provide compliance management tools such as for respiratory pressure therapy. In some versions, a respiratory pressure therapy system may include one or more processors, such as of a data server, configured to communicate with a computing device and/or a respiratory pressure therapy device. The respiratory pressure therapy device may be configured to deliver respiratory pressure therapy to a patient for a session. The computing device may be associated with the patient. The processor(s)

(Continued)

may be further configured to compute a therapy quality indicator of the session from usage data relating to the session. The therapy quality indicator may be a number derived from contributions of a plurality of usage variables for the session in the usage data. The processor(s) may be further configured to present, such as by transmitting, the therapy quality indicator to the computing device. The therapy quality indicator may promote patient compliance.

23 Claims, 15 Drawing Sheets

Related U.S. Application Data

(60) Provisional application No. 62/068,062, filed on Oct. 24, 2014.

(51) Int. Cl.
*A61M 16/00* (2006.01)
*A61M 16/10* (2006.01)
*A61M 16/16* (2006.01)
*G16H 20/40* (2018.01)

(52) U.S. Cl.
CPC .......... *A61B 5/08* (2013.01); *A61M 16/0051* (2013.01); *A61M 16/0069* (2014.02); *A61M 16/024* (2017.08); *A61M 16/107* (2014.02); *A61M 16/16* (2013.01); *G16H 20/40* (2018.01); *A61M 2205/15* (2013.01); *A61M 2205/3344* (2013.01); *A61M 2205/3553* (2013.01); *A61M 2205/3584* (2013.01); *A61M 2205/3592* (2013.01); *A61M 2205/42* (2013.01); *A61M 2205/502* (2013.01); *A61M 2205/583* (2013.01); *A61M 2230/40* (2013.01); *Y02A 90/10* (2018.01)

(58) Field of Classification Search
CPC .............. A61M 16/024; A61M 16/026; A61M 16/0633; A61M 16/107; A61M 16/12; A61M 16/16; A61M 2016/0018; A61M 2016/0027; A61M 2016/0036; A61M 2202/0208; A61M 2205/18; A61M 2205/21; A61M 2205/33; A61M 2205/35–3592; A61M 2205/42; A61M 2205/50; A61M 2205/502; A61M 2205/505; A61M 2205/52; A61B 5/08; A61B 5/0816; A61B 5/0826; A61B 5/087; A61B 5/0871; A61B 2560/0266
See application file for complete search history.

(56) References Cited

U.S. PATENT DOCUMENTS

| | | |
|---|---|---|
| 6,532,959 B1 | 3/2003 | Berthon-Jones |
| 7,890,342 B1 | 2/2011 | Yruko et al. |
| 9,463,294 B2 | 10/2016 | Laura Lapoint et al. |
| 2005/0061315 A1 | 3/2005 | Lee et al. |
| 2005/0188991 A1 | 9/2005 | Sun et al. |
| 2006/0276718 A1 | 12/2006 | Madaus et al. |
| 2010/0049008 A1 | 2/2010 | Doherty |
| 2010/0268304 A1 | 10/2010 | Matos |
| 2010/0275921 A1 | 11/2010 | Schindhelm et al. |
| 2012/0012110 A1* | 1/2012 | Bassin ............... A61M 16/20 128/204.23 |
| 2013/0269700 A1 | 10/2013 | Laura Lapoint et al. |
| 2013/0284177 A1 | 10/2013 | Li et al. |
| 2013/0340751 A1 | 12/2013 | D'Angelo et al. |
| 2014/0249760 A1 | 8/2014 | Proud et al. |

FOREIGN PATENT DOCUMENTS

| | | |
|---|---|---|
| CN | 102920543 A | 2/2013 |
| CN | 102961140 A | 3/2013 |
| CN | 103313747 A | 9/2013 |
| CN | 103370005 A | 10/2013 |
| JP | 200652 7 A | 8/2006 |
| JP | 2014503289 A | 2/2014 |
| WO | 2004082751 A1 | 9/2004 |
| WO | 2006133493 A1 | 12/2006 |
| WO | 2010104978 A2 | 9/2010 |
| WO | 2012085756 A1 | 6/2012 |
| WO | 2012095764 A1 | 7/2012 |
| WO | 2012171072 A1 | 12/2012 |

OTHER PUBLICATIONS

International Search Report for Application No. PCT/AU2015/050655, dated Jan. 18, 2016.
JP Notice of Allowance issued Feb. 3, 2021 for JP Application No. 2017-522043.
Notification of Grant issued in corresponding CN Application No. 201580069094.0 dated Aug. 28, 2020.
The Supplementary European Search Report Including Written Opinion for EP Application No. 15853569, dated May 28, 2018.
West, John B, "Respiratory Physiology", Lippincott Williams & Wilkins, 9th edition published 2011.
Extended European Search Report for Application No. EP21205432 dated May 18, 2022.
Office Action issued in corresponding Japanese Patent Application No. 2022-066190, mailed Jan. 6, 2023, 8 pages.

* cited by examiner

RESPIRATORY PRESSURE THERAPY SYSTEM

1. CROSS-REFERENCE TO RELATED APPLICATIONS

The present application is a continuation of U.S. application Ser. No. 15/520,663, filed on Apr. 20, 2017, which is a national phase entry under 35 U.S.C. § 371 of International Application No. PCT/AU2015/050655, filed Oct. 23, 2015, published in English, which claims the benefit of and priority from U.S. Provisional Application No. 62/068,062, filed Oct. 24, 2014, all of which are incorporated herein by reference.

2. STATEMENT REGARDING FEDERALLY SPONSORED RESEARCH OR DEVELOPMENT

Not Applicable

3. THE NAMES OF PARTIES TO A JOINT RESEARCH DEVELOPMENT

Not Applicable

4. SEQUENCE LISTING

Not Applicable

5. BACKGROUND OF THE TECHNOLOGY

5.1 Field of the Technology

The present technology relates to one or more of the detection, diagnosis, treatment, prevention and amelioration of respiratory-related disorders. The present technology also relates to medical devices or apparatus, and their use.

5.2 Description of the Related Art 5.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

A range of therapies have been used to treat or ameliorate such conditions. Furthermore, otherwise healthy individuals may take advantage of such therapies to prevent respiratory disorders from arising.

5.2.2 Therapy

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive, or aesthetically unappealing.

Pressure support ventilation provides ventilatory support to a patient through the upper airways to assist the patient in taking a full breath and/or maintain adequate oxygen levels in the body by doing some or all of the work of breathing. The ventilatory support is provided via a patient interface. Pressure support ventilation has been used to treat CSR.

CPAP therapy and pressure support ventilation therapy may be grouped under the heading of respiratory pressure therapy (RPT).

5.2.3 Diagnosis and Therapy Systems

Respiratory pressure therapy may be provided by a respiratory pressure therapy system or device. Therapy systems and devices may also be used to diagnose a condition without treating the condition.

A respiratory pressure therapy system may comprise a respiratory pressure therapy device (RPT device), an air circuit, a humidifier, a patient interface, and data management.

5.2.3.1 Patient Interface

A patient interface may be used to interface respiratory equipment to its user, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 cmH$_2$O.

5.2.3.2 Respiratory Pressure Therapy Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for non-dependent ventilation for a range of patients for treating a number of respiratory disorders.

The ResMed Elisée™ 150 ventilator and ResMed VS III™ ventilator may provide support for dependent ventilation suitable for adult or paediatric patients for treating a number of respiratory disorders. These ventilators provide volumetric and barometric ventilation modes with a single or double limb circuit.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

5.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

5.2.3.4 Data Management

Insurance companies, or other reimbursing entities, often require evidence that the patient prescribed with respiratory therapy has been "compliant", that is, used their RPT device according to certain a "compliance rule" before reimbursing the patient for the RPT device. One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify the reimbursing entity that the patient is compliant. This process can be costly, time-consuming, and error-prone if conducted manually. RPT devices typically therefore contain data management capability that enables the device to store and transmit therapy variable data to a remote server to determine whether the patient has used the RPT device according to the compliance rule.

5.2.4 Compliance Problems

Studies have shown that up to 90% of patients prescribed with respiratory pressure therapy have at least some problems meeting compliance rules. Difficulty in setting up an RPT device, discomfort due to an ill-fitting or ill-adjusted patient interface, lack of tolerance for the sensation of positive airway pressure at the prescribed level, excessive leaks causing noise or disruption to the patient or their bed partner, and lack of improvement in subjective well-being are all examples of such problems. Many patients simply give up after early difficulties, and some may seek assistance from their health care provider. Even those patients who are initially compliant may not persist with therapy due to a lack of subjective improvement in their condition.

A need therefore exists for a respiratory pressure therapy system that encourages compliance with prescribed respiratory pressure therapy.

6. BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of the present technology relates to methods and/or systems that encourage patients to comply with respiratory pressure therapy. This is achieved by providing patients with a simple and meaningful indicator of the quality of the therapy they are receiving. This indicator serves to increase and sustain their motivation to continue with their therapy.

Optionally, analysis of the therapy quality indicator may form the basis on which to improve the patient's therapy. The improvement may take the form of a change to the therapy mode or therapy device settings. The improvement may also take the form of prompting the patient to take some action, e.g. adjust their mask fit.

Some versions of the present technology may include a respiratory pressure therapy system. The system may include a data server configured to communicate with a computing device and a respiratory pressure therapy device. The respiratory pressure therapy device may be configured to deliver respiratory pressure therapy to a patient for a session. The computing device may be associated with the patient. The data server may be further configured to compute a therapy quality indicator of the session from usage data relating to the session. The therapy quality indicator may be a number derived from contributions of a plurality of usage variables for the session in the usage data. The data server may be further configured to transmit the therapy quality indicator to the computing device.

In some versions, the data server may be further configured to receive the usage data from the respiratory pressure therapy device. The data server may be further configured to receive therapy data relating to the session from the respiratory pressure therapy device, and to compute the usage data from the therapy data. The data server may be further configured to receive the usage data from the patient computing device. The data server may be further configured to receive therapy data relating to the session from the patient computing device, and to compute the usage data from the therapy data.

In some versions, the data server may be further configured to apply one or more rules to the therapy quality indicator, and take an action to improve the patient's respiratory pressure therapy. The action may include altering a setting of the respiratory pressure therapy device. The action may include changing a therapy mode of the respiratory pressure therapy device. The action may include sending a message to the computing device. The message may prompt the patient to adjust fitting of a patient interface through which the respiratory pressure therapy is being delivered. The data server may be further configured to issue a query to the computing device, wherein the action is based on a response to the query.

Some versions of the present technology may include a method of providing to or monitoring respiratory pressure therapy of a patient. The method may include computing a therapy quality indicator of a session of respiratory pressure therapy from usage data relating to the session. The therapy quality indicator may be a number derived from contributions of a plurality of usage variables for the session in the usage data. The method may include transmitting the therapy quality indicator to a computing device associated with the patient. In some versions, the system may further include one or more of the respiratory pressure therapy device and the computing device.

In some versions, the method may include computing the usage data from therapy data relating to the session. The usage variables may include two or more of a group consisting of: usage time of the session; apnea-hypopnea index for the session; average leak flow rate for the session; average mask pressure for the session; number of sub-sessions within the session; and whether the session is a compliant session according to a compliance rule. The computing may involve computing a sum of the contributions of the respective usage variables. A contribution thereof may be proportional to a difference between a usage variable and a threshold for the usage variable. A contribution thereof may be a maximum contribution if the usage variable exceeds a maximum threshold for the usage variable. A contribution thereof may be a minimum contribution if the usage variable is less than a minimum threshold for the usage variable. A contribution thereof may be a minimum contribution if the usage variable exceeds a maximum threshold for the usage variable. A contribution thereof may be a maximum contribution if the usage variable is less than a minimum threshold for the usage variable. In some versions, the contributions of all but one usage variable may be reduced in proportion to a ratio of the contribution of the other usage variable to a maximum contribution for that usage variable. Optionally, a bonus or penalty may be applied to a contribution of a usage variable based on a value of the usage variable in relation to a recent history of the usage variable.

In some cases, the transmitting may involve sending an email containing the therapy quality indicator to the computing device. The transmitting may involve sending an SMS message containing the therapy quality indicator to the computing device. The transmitting may involve sending a notification containing the therapy quality indicator to the computing device. The transmitting may involve sending a web page containing the therapy quality indicator to the computing device. The method may further include transmitting the contributions from the respective usage variables to the computing device.

In some cases, the method may include applying one or more rules to the therapy quality indicator, and taking an action to improve the patient's respiratory pressure therapy. The taking of the action may include altering a setting of a respiratory pressure therapy device. The taking of the action may include changing a therapy mode of a respiratory pressure therapy device. The taking of the action may include sending a message to the computing device. The message may prompt the patient to adjust fitting of a patient interface through which the respiratory pressure therapy is being delivered. The method may include issuing a query to the computing device, wherein the action is based on a response to the query.

Some versions of the present technology may include a respiratory pressure therapy compliance apparatus. The apparatus may include one or more processors configured to access data associated with usage of a respiratory pressure therapy device that delivers a respiratory pressure therapy to a patient in multiple sessions. The one or more processors may be further configured to determine a therapy quality indicator of a session of the multiple sessions from usage data relating to the session. The therapy quality indicator may be a number derived from contributions of a plurality of usage variables for the session in the usage data. The one or more processors may be further configured to present the therapy quality indicator.

In some versions, the usage variables may include any one, two or more of a group consisting of: usage time of the session; apnea-hypopnea index for the session; average leak flow rate for the session; average mask pressure for the session; number of sub-sessions within the session; and whether the session is a compliant session according to a compliance rule. The determination of the therapy quality indicator by the apparatus may include computing a sum of the contributions of the respective usage variables. In some such cases, a contribution may be proportional to a difference between a usage variable and a threshold for the usage variable. In some such cases, a contribution may be a maximum contribution if the usage variable exceeds a maximum threshold for the usage variable. In some such cases, a contribution may be a minimum contribution if the usage variable is less than a minimum threshold for the usage variable. In some such cases, a contribution may be a minimum contribution if the usage variable exceeds a maximum threshold for the usage variable. In some such cases, a contribution may be a maximum contribution if the usage variable is less than a minimum threshold for the usage variable. The contributions of all but one usage variable may be reduced in proportion to a ratio of the contribution of the other usage variable to a maximum contribution for that usage variable. Optionally, the one or more processors may be further configured to apply a bonus or penalty to a contribution of a usage variable based on a value of the usage variable in relation to a recent history of the usage variable.

Some versions of the present technology may include a method for providing respiratory pressure therapy compliance information. The method may involve, in one or more processors, computing a therapy quality indicator of a session of respiratory pressure therapy from usage data relating to the session, wherein the therapy quality indicator is a number derived from contributions from a plurality of usage variables for the session in the usage data; and presenting, with the one or more processors, the therapy quality indicator. The presenting may involve transmitting the therapy quality indicator to a computing device associated with a patient for display to the patient.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7. BRIEF DESCRIPTION OF THE DRAWINGS

The present technology is illustrated by way of example, and not by way of limitation, in the figures of the accompanying drawings, in which like reference numerals refer to similar elements including:

7.1 Therapy Systems

FIG. 1 shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

7.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

7.3 Patient Interface

FIG. 3 shows a patient interface in the form of a nasal mask in accordance with one form of the present technology.

7.4 RPT Device

7.5 Humidifier

Figure 5A:
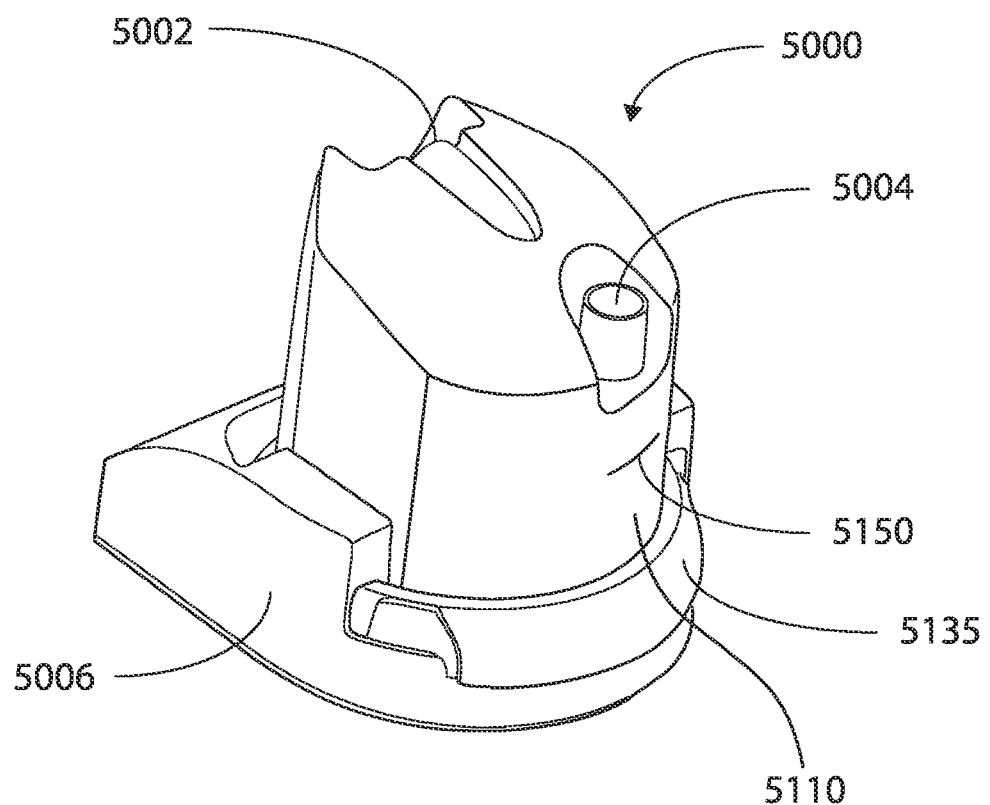

FIG. 5A shows an isometric view of a humidifier in accordance with one form of the present technology.

Figure 5B:
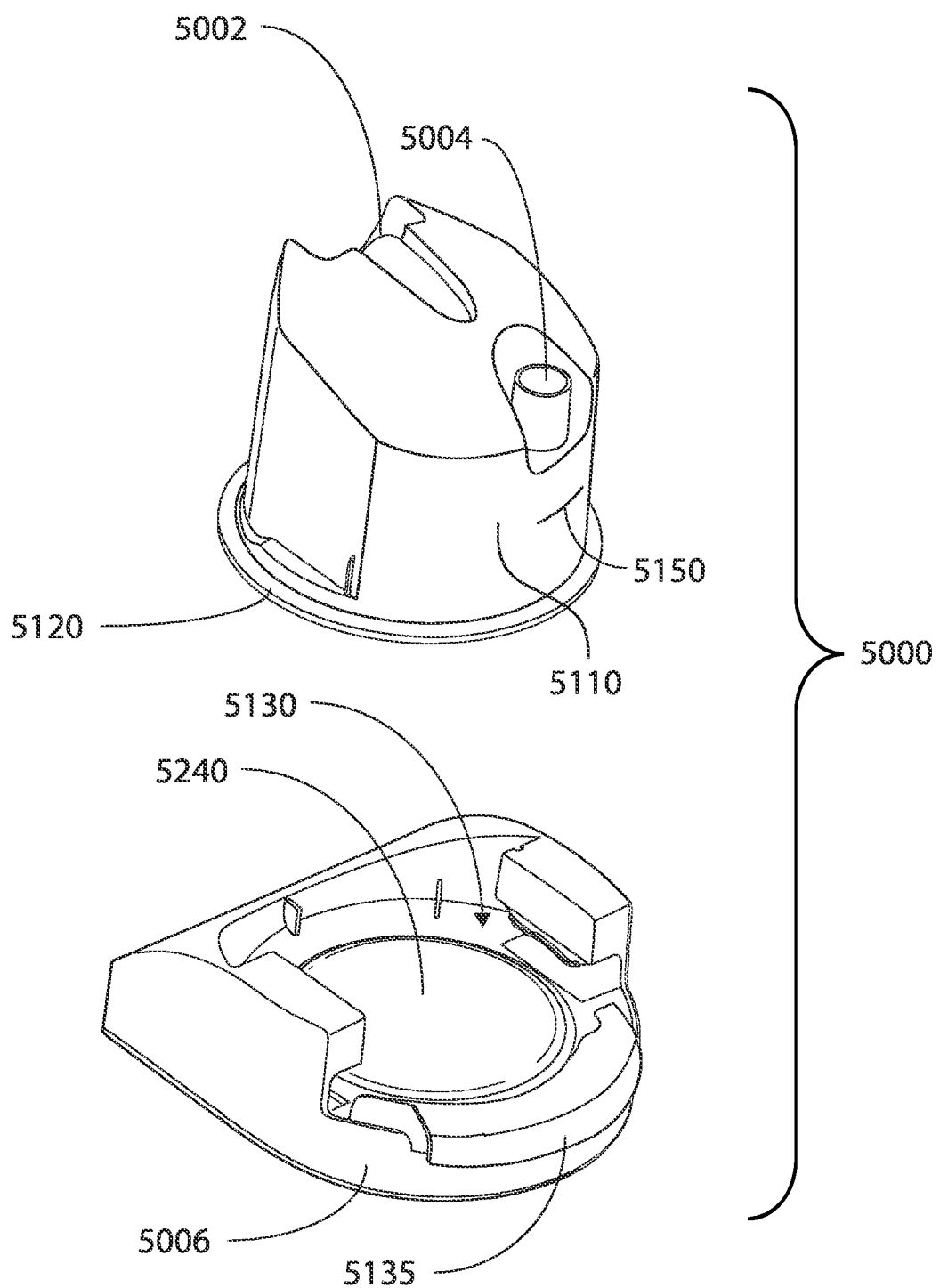

FIG. 5B shows an isometric view of a humidifier in accordance with one form of the present technology, showing a humidifier reservoir 5110 removed from the humidifier reservoir dock 5130.

Figure 5C:
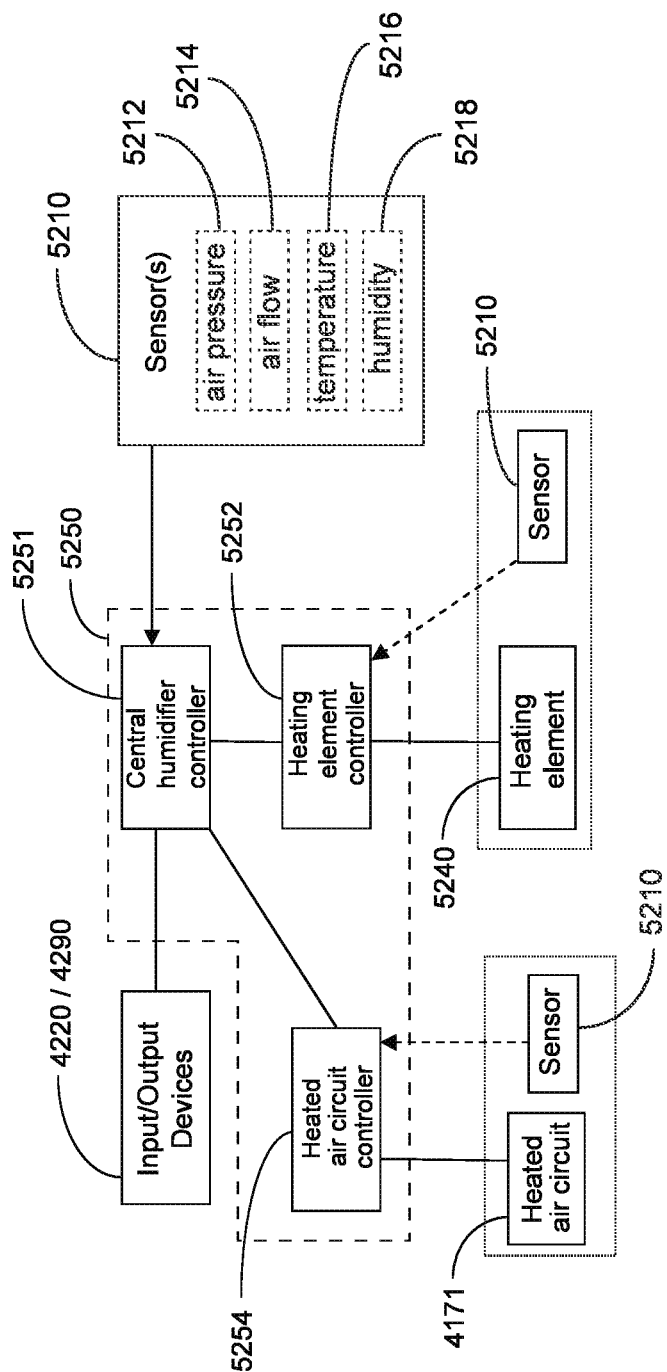

FIG. 5C shows a schematic of a humidifier in accordance with one form of the present technology.

7.6 Breathing Waveforms

Figure 6:
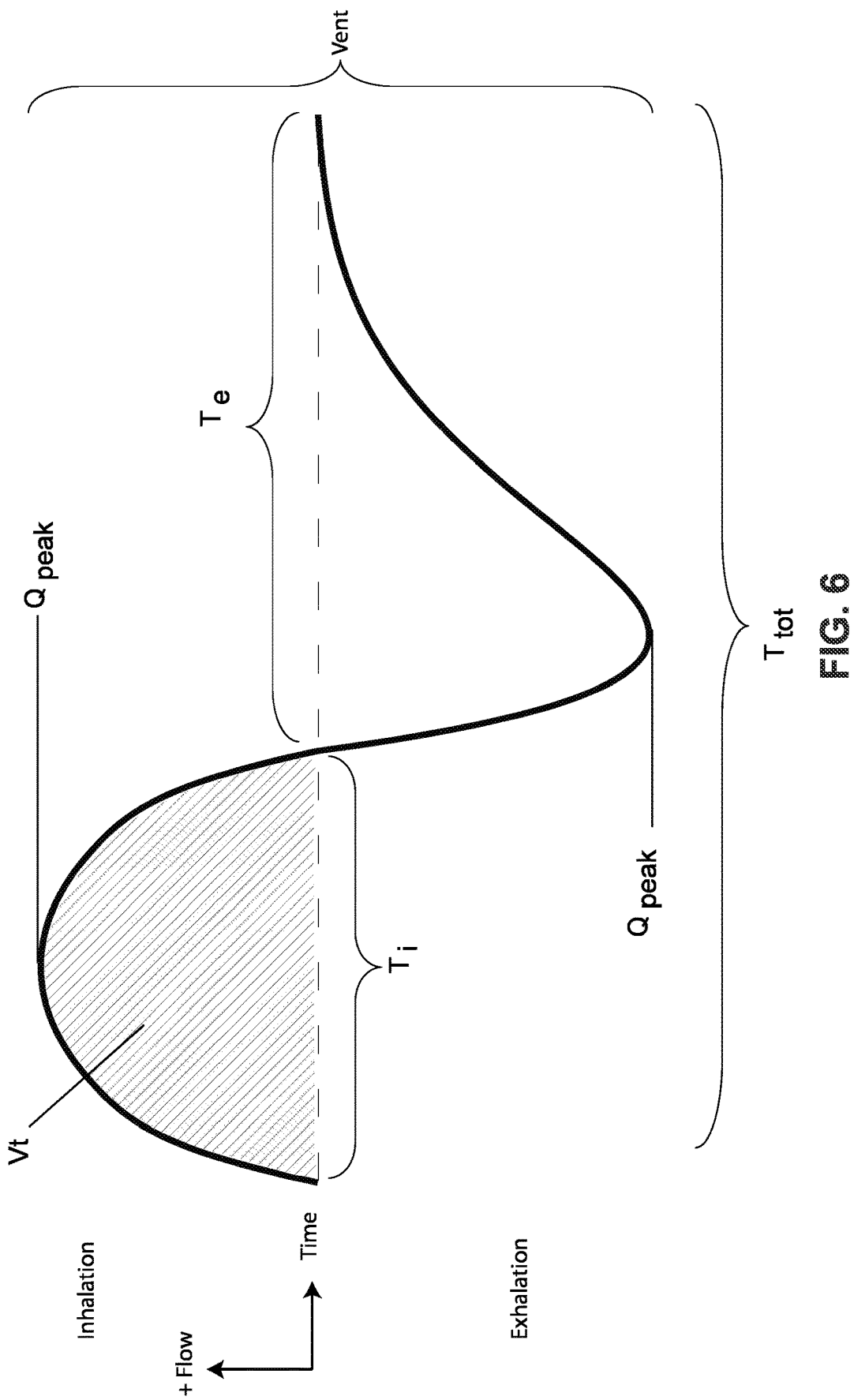

FIG. 6 shows a model typical breath waveform of a person while sleeping.

7.7 Respiratory Pressure Therapy System

Figure 7A:
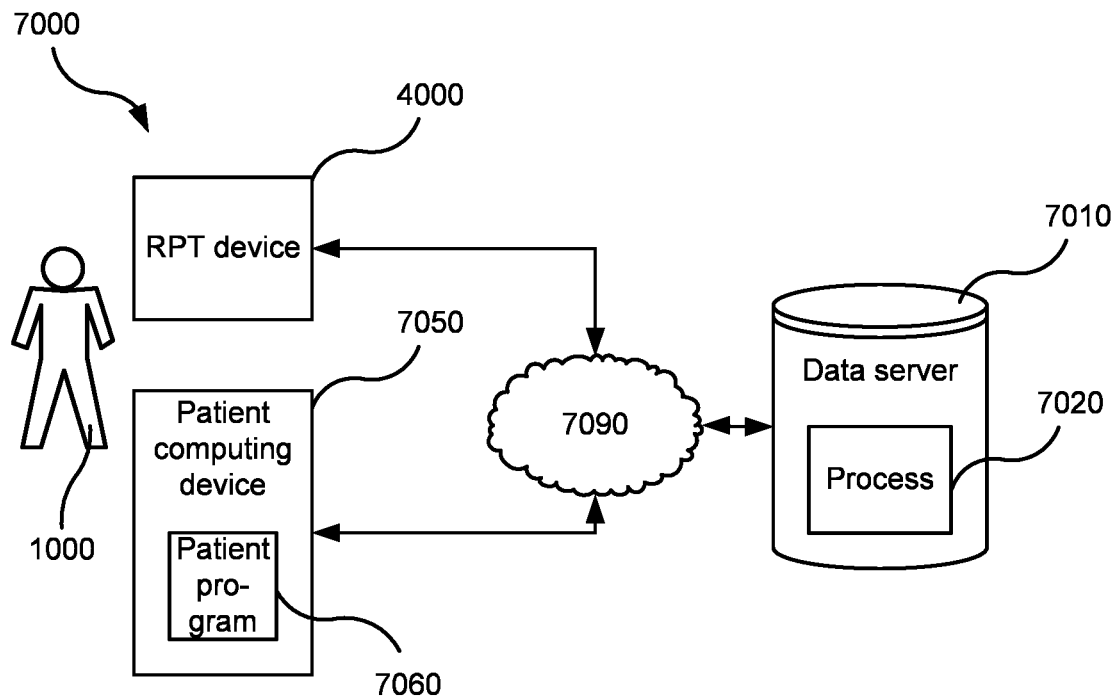

FIG. 7A is a block diagram illustrating a respiratory pressure therapy system according to one implementation of the present technology.

Figure 7B:
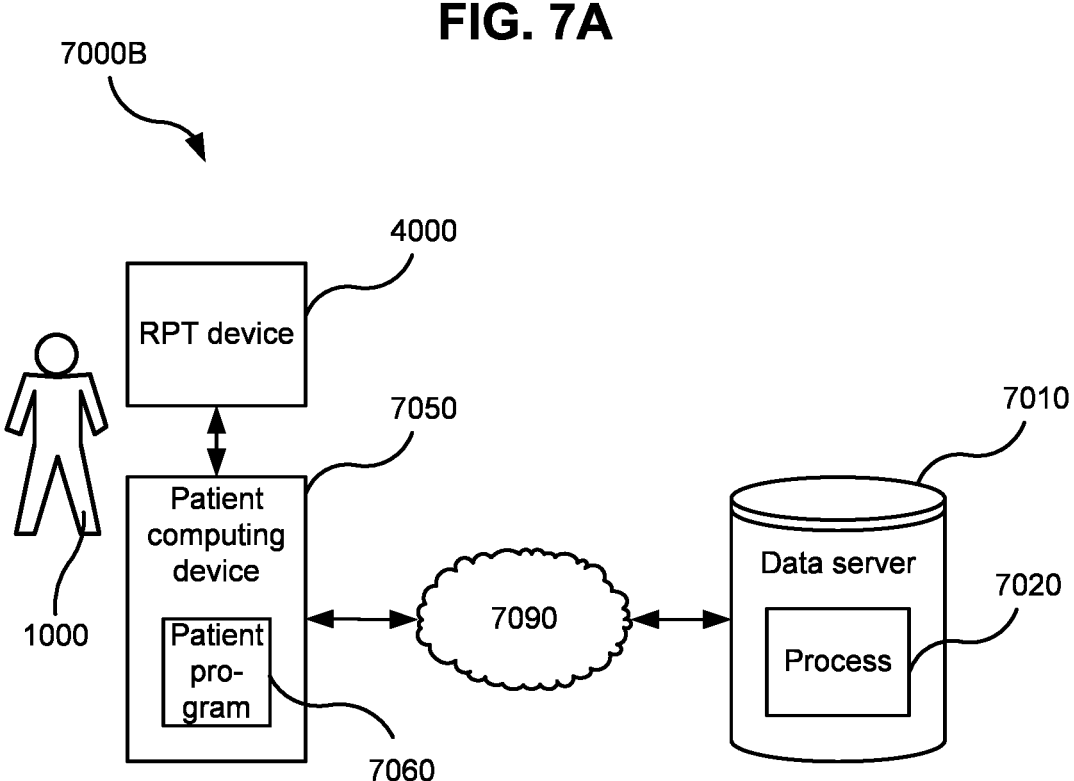

FIG. 7B is a block diagram illustrating a respiratory pressure therapy system according to another implementation of the present technology.

Figure 8:
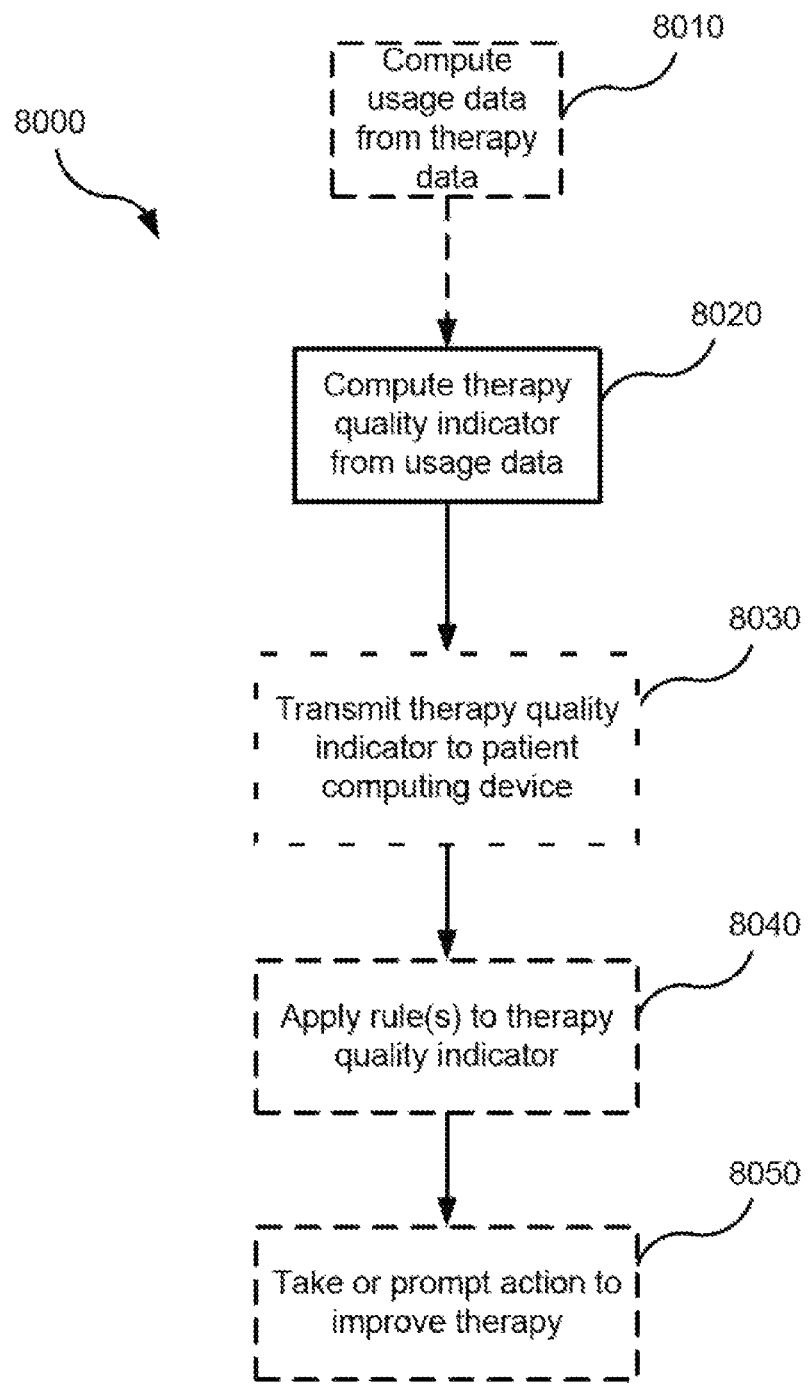

FIG. 8 is a block diagram illustrating a method carried out by the data server in the respiratory pressure therapy system of FIG. 7A or FIG. 7B in one form of the present technology.

Figure 9:
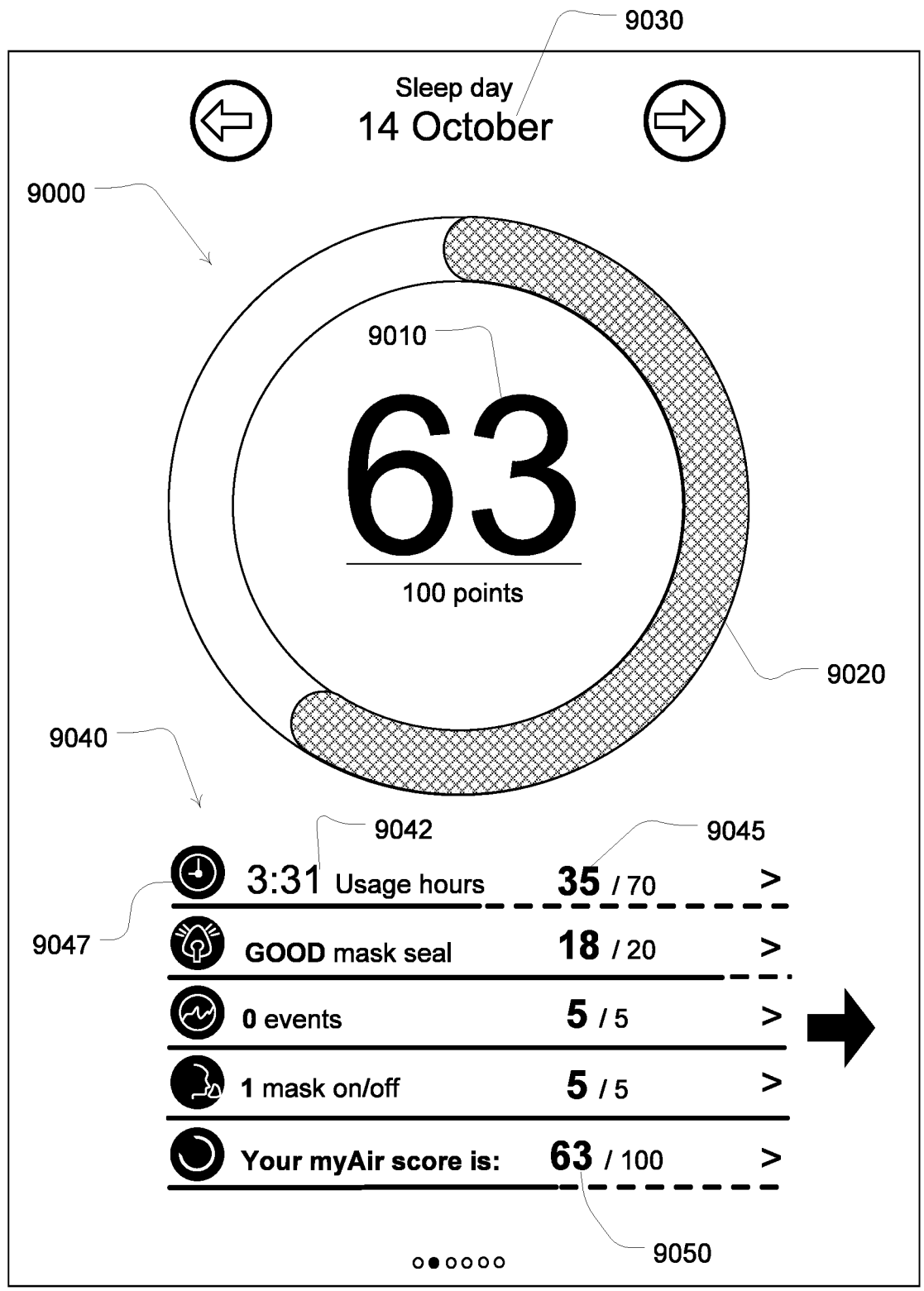

FIG. 9 is an example image illustrating the therapy quality indicator and other information in one implementation of the method of FIG. 8.

Figure 10:
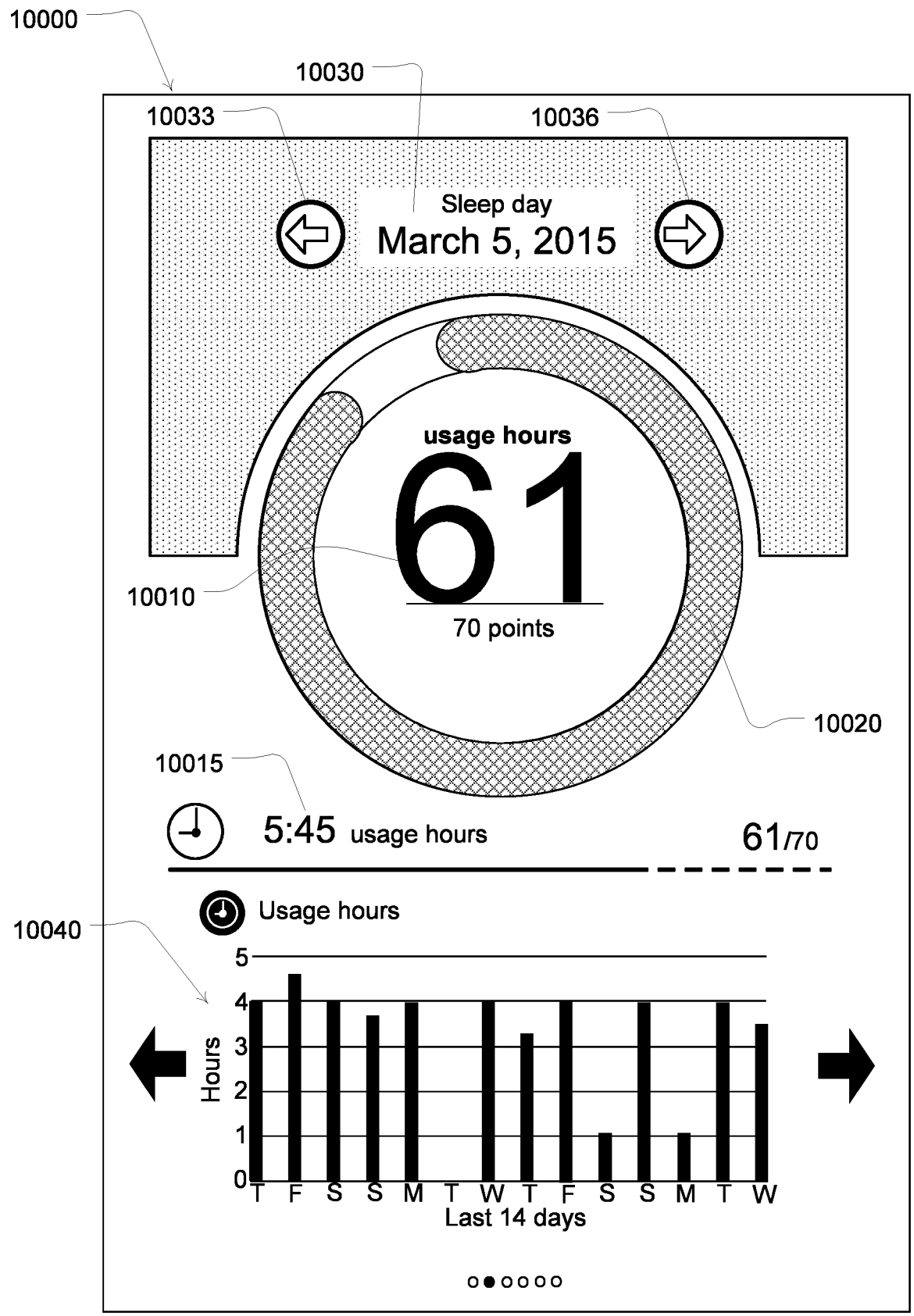

FIG. 10 is an example image illustrating the history of a usage variable in one implementation of the method of FIG. 8.

Figure 11:
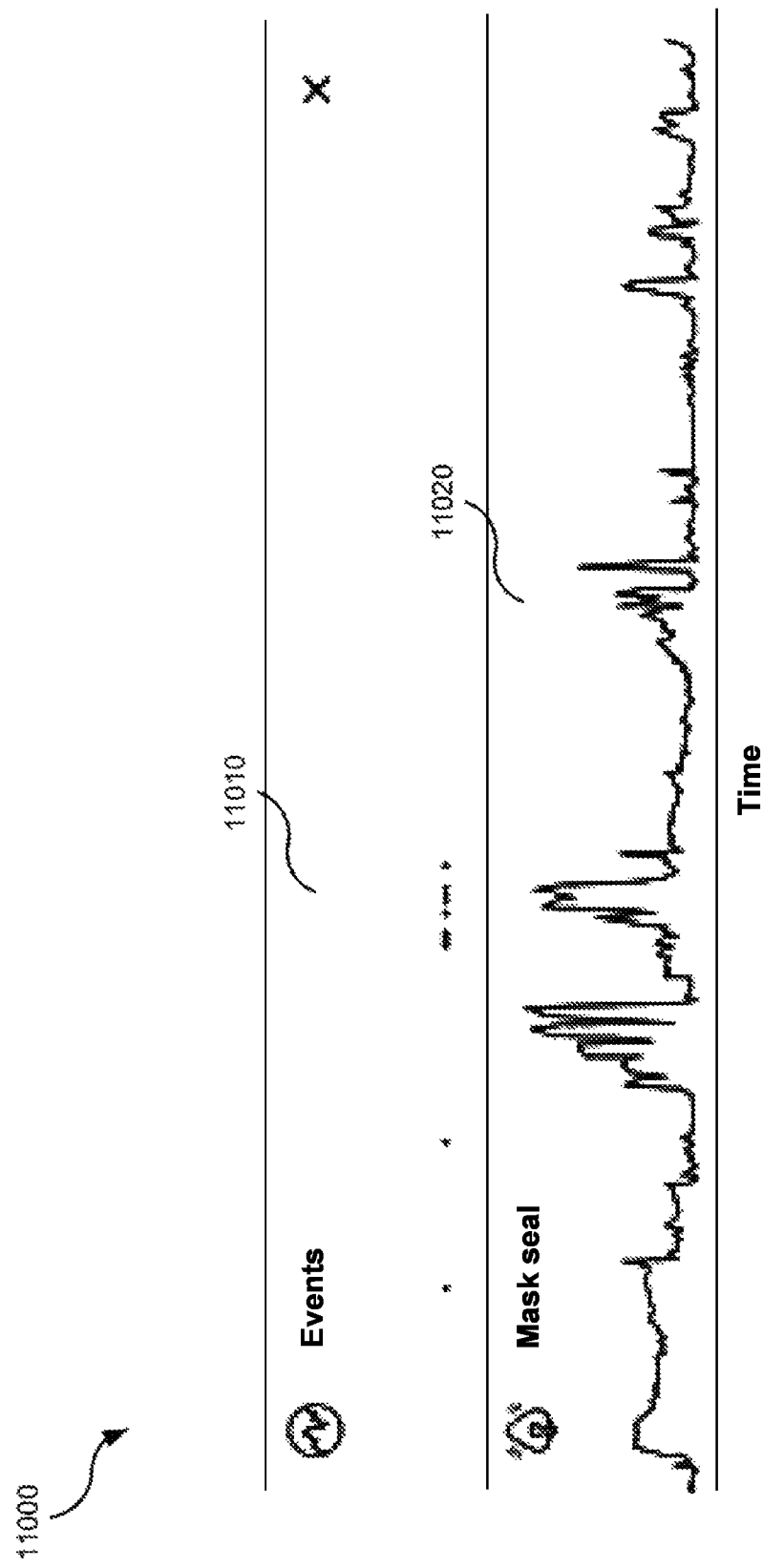

FIG. 11 is an example image illustrating therapy data from a respiratory pressure therapy session in one implementation of the method of FIG. 8.

8. DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

8.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

8.2 Therapy Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

8.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

8.4 RPT Device

An RPT device 4000 in accordance with one aspect of the present technology comprises mechanical and pneumatic components 4100, electrical components 4200 and is configured to execute one or more algorithms. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

In one form of the present technology, the central controller 4230 executes one or more algorithms for the determination of one or more respiratory pressure therapy parameters.

In one form of the present technology, the respiratory pressure therapy parameter is an instantaneous treatment pressure Pt. In one implementation of this form, the central controller 4230 determines the treatment pressure Pt using the equation $$Pt = AP(\Phi) + P_0 \quad (1)$$

where:
A is an amplitude,
P ($\Phi$) is a pressure-phase waveform value (in the range 0 to 1) at a current value $\Phi$ of phase of the respiratory cycle, and
$P_0$ is a base pressure.

The values of the amplitude A and the base pressure $P_0$ may be set by the central controller 4230 depending on the chosen respiratory pressure therapy mode in the manner described below.

Determination of treatment pressure according to equation (1) may be subject to minimum and maximum limits Pmin and Pmax respectively.

8.5 Respiratory Pressure Therapy Modes

Various respiratory pressure therapy modes may be implemented by the RPT device 4000 depending on the values of the parameters A and $P_0$ in the treatment pressure equation (1) used by the central controller 4230 in one form of the present technology.

8.5.1 CPAP Therapy

In some implementations of this form of the present technology, the amplitude A is identically zero, so the treatment pressure Pt is identically equal to the base pressure $P_0$ throughout the respiratory cycle. Such implementations are generally grouped under the heading of CPAP therapy. In such implementations, there is no need for a pressure-phase waveform P($\Phi$).

In CPAP therapy modes, the base pressure $P_0$ may be a constant value that is hard-coded or manually entered to the RPT device 4000. This alternative is sometimes referred to as constant CPAP therapy. The constant value for the base pressure $P_0$ may be selected for a given patient via a process known as titration. During titration, a clinician typically adjusts the treatment pressure Pt in response to observations of flow limitation, apnea, hypopnea, patency, and snore during a titration session. The titrated base pressure $P_0$ may be then computed as a statistical summary of the treatment pressure Pt during the titration session.

Alternatively, the central controller 4230 may continuously compute the base pressure $P_0$ during CPAP therapy. In one such implementation, the central controller 4230 continuously computes the base pressure $P_0$ as a function of indices or measures of sleep disordered breathing, such as one or more of flow limitation, apnea, hypopnea, patency, and snore. This alternative is sometimes referred to as APAP therapy. Because the continuous computation of the base pressure $P_0$ resembles the manual adjustment of the treatment pressure Pt by a clinician during titration, APAP therapy is also sometimes referred to as auto-titrating CPAP.

8.5.2 Pressure Support Ventilation therapy
8.5.3 Bi-Level Therapy

In other implementations of this form of the present technology, the value of amplitude A in equation (1) may be positive. Such implementations are known as bi-level therapy, because in determining the treatment pressure Pt using equation (1) with positive amplitude A, the central controller 4230 oscillates the treatment pressure Pt between two values or levels in synchrony with the spontaneous respiratory effort of the patient 1000. That is, the central controller 4230 increases the treatment pressure Pt to $P_0$+A (known as the IPAP) at the start of, or during, or inspiration and decreases the treatment pressure Pt to the base pressure $P_0$ (known as the EPAP) at the start of, or during, expiration.

In some forms of bi-level therapy, the IPAP is a treatment pressure that has the same purpose as the treatment pressure in CPAP therapy modes, and the EPAP is the IPAP minus the amplitude A, which has a "small" value (a few cmH$_2$O) sometimes referred to as the Expiratory Pressure Relief (EPR). Such forms are sometimes referred to as CPAP therapy with EPR, which is generally thought to be more comfortable than straight CPAP therapy. In CPAP therapy with EPR, any or all of the IPAP, the EPAP, and the EPR may be constant values that are hard-coded or manually entered to the RPT device 4000. Alternatively, the central controller 4230 may continuously compute the IPAP and/or the EPAP during CPAP with EPR. In one such implementation, the central controller 4230 may continuously compute the EPAP, the IPAP, and/or the EPR as a function of indices or measures of sleep disordered breathing in analogous fashion to the computation of the base pressure $P_0$ in APAP therapy described above.

In other forms of bi-level therapy, the amplitude A is large enough that the RPT device 4000 does some or all of the work of breathing of the patient 1000. In such forms, known as pressure support ventilation therapy, the amplitude A is referred to as the pressure support, or swing. In pressure support ventilation therapy, the IPAP is the base pressure $P_0$ plus the pressure support A, and the EPAP is the base pressure $P_0$.

In some forms of pressure support ventilation therapy, known as fixed pressure support ventilation therapy, the pressure support A is fixed at a predetermined value, e.g. 10 cmH$_2$O. The predetermined pressure support value is a setting of the RPT device 4000, and may be set for example by hard-coding during configuration of the RPT device 4000 or by manual entry through the input device 4220.

One form of pressure support ventilation therapy is known as "paced breathing". Paced breathing comprises the use of pressure support ventilation to slow down a patient's breathing toward an "optimal" breathing rate in a manner that is sympathetic to the response of the patient such that the therapy is well tolerated. It is established that slow-paced breathing can be calming, particularly in patients who are sympathetically over-active, such as patients suffering from insomnia.

8.6 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

8.6.1 Humidifier Mechanical Components
8.6.1.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory pressure therapy session, such as one night of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

8.6.1.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

8.6.1.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

8.6.1.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a caregiver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

8.6.2 Humidifier Electrical & Thermal Components

The humidifier 5000 may comprise a number of electrical and/or thermal components such as those listed below.

8.6.2.1 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

8.6.2.1.1 Pressure Transducer

One or more pressure transducers 5212 may be provided to the humidifier 5000 in addition to, or instead of, a pressure sensor 4272 provided in the RPT device 4000.

8.6.2.1.2 Flow Rate Transducer

One or more flow rate transducers 5214 may be provided to the humidifier 5000 in addition to, or instead of, a flow rate sensor 4274 provided in the RPT device 4000.

8.6.2.1.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

8.6.2.1.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

8.6.2.2 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

8.6.2.3 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

8.7 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

8.8 Respiratory Pressure Therapy Systems

8.8.1 System Architecture

Figure 1:
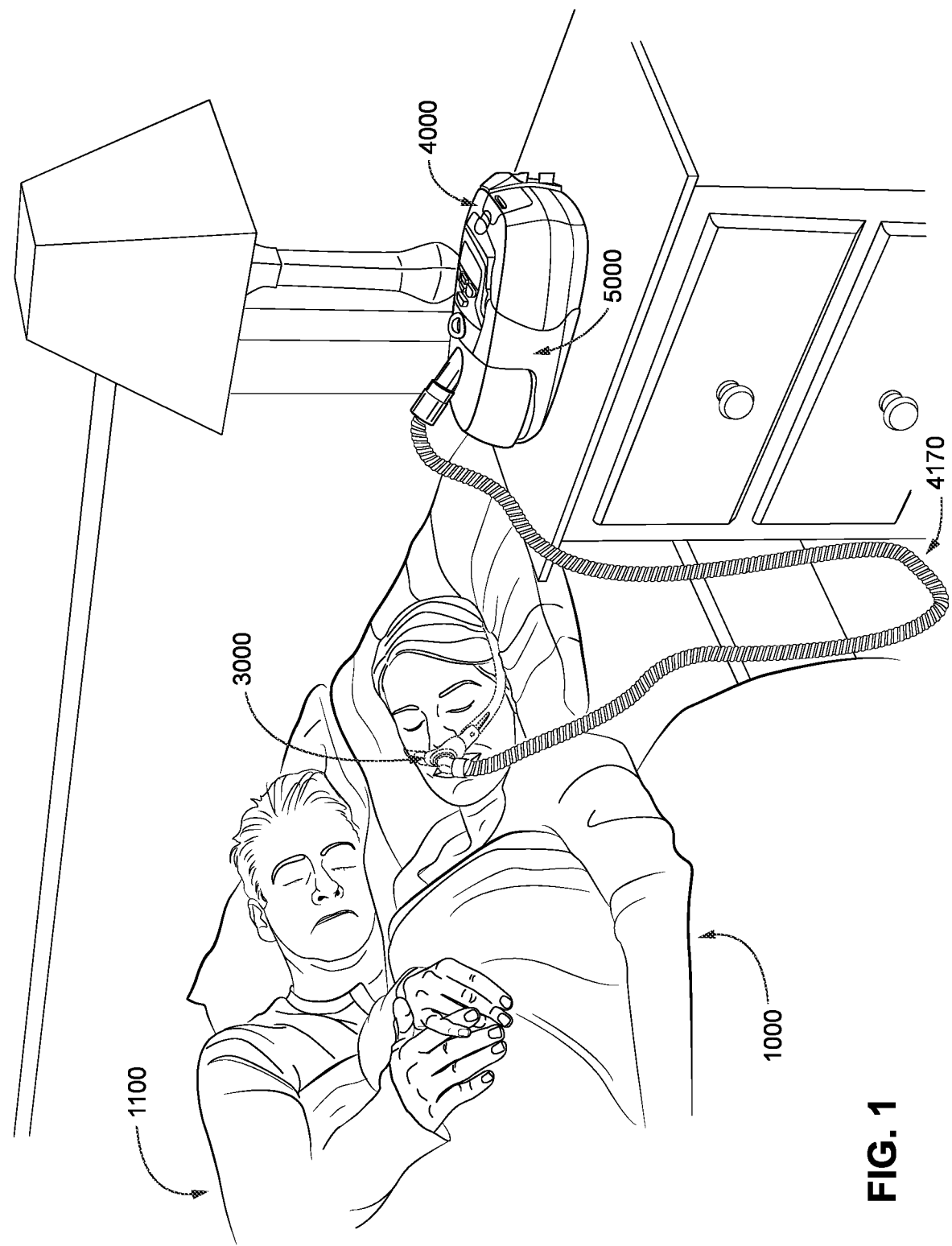
Figure 2:
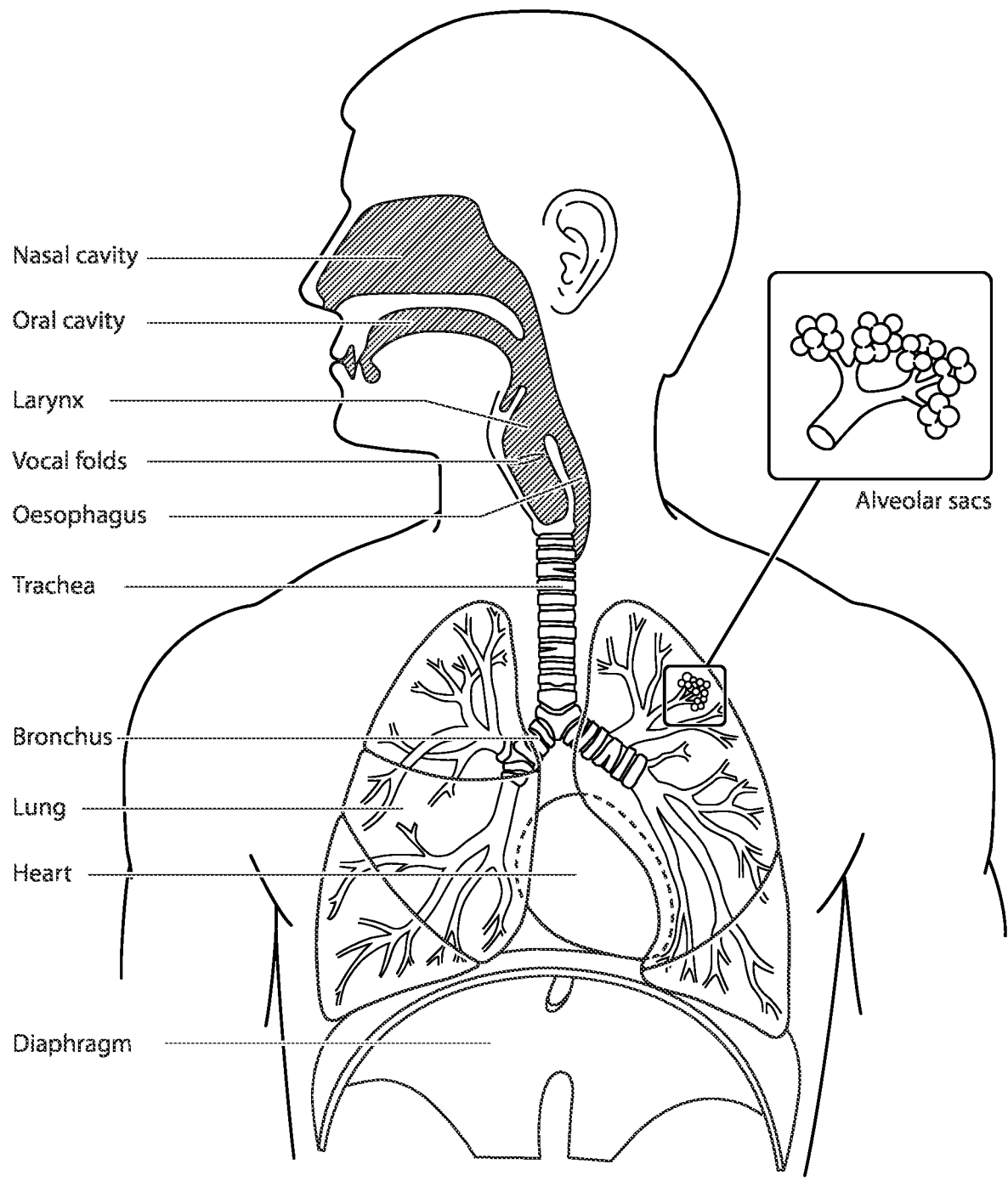
Figure 3:
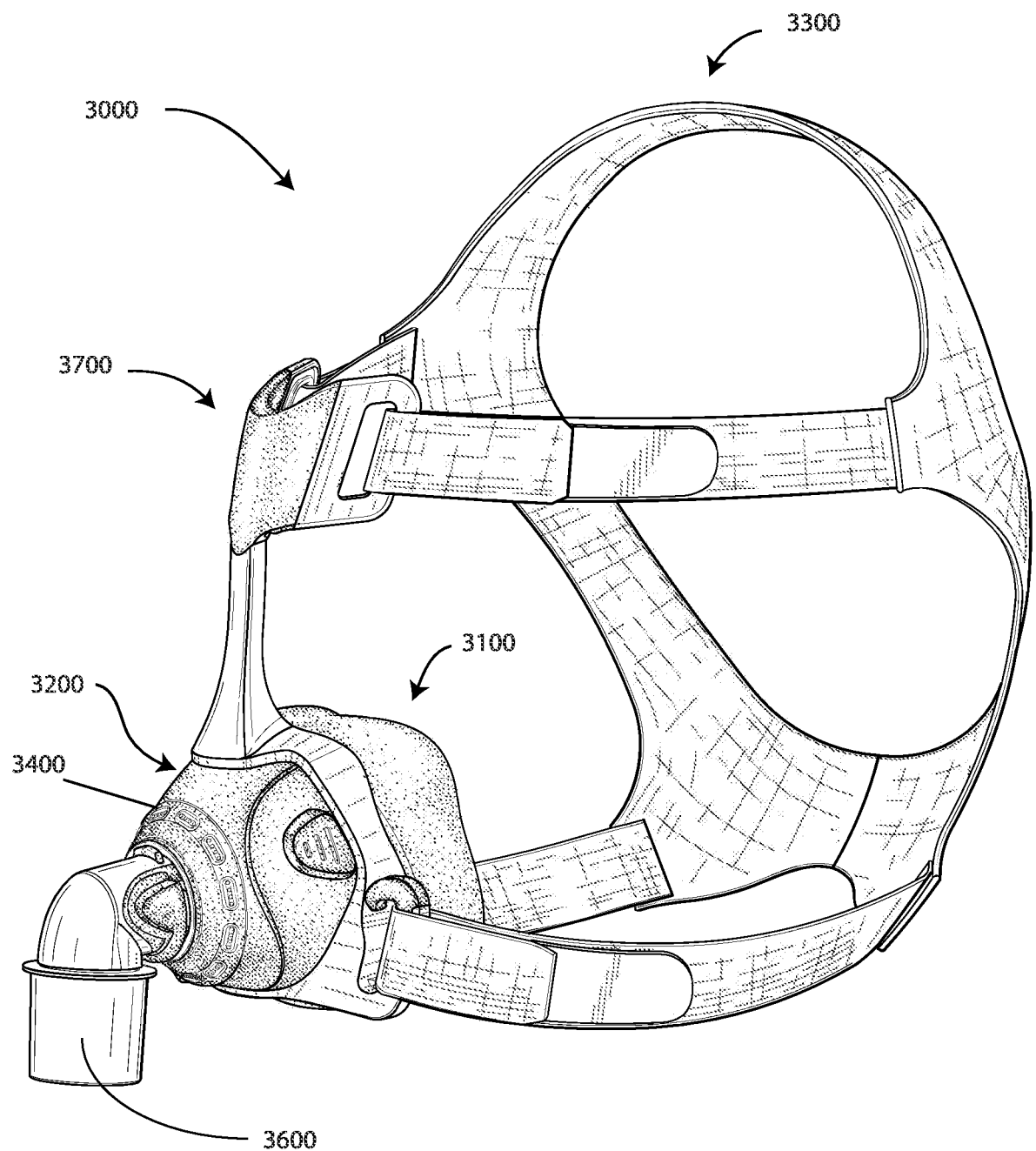
Figure 4A:
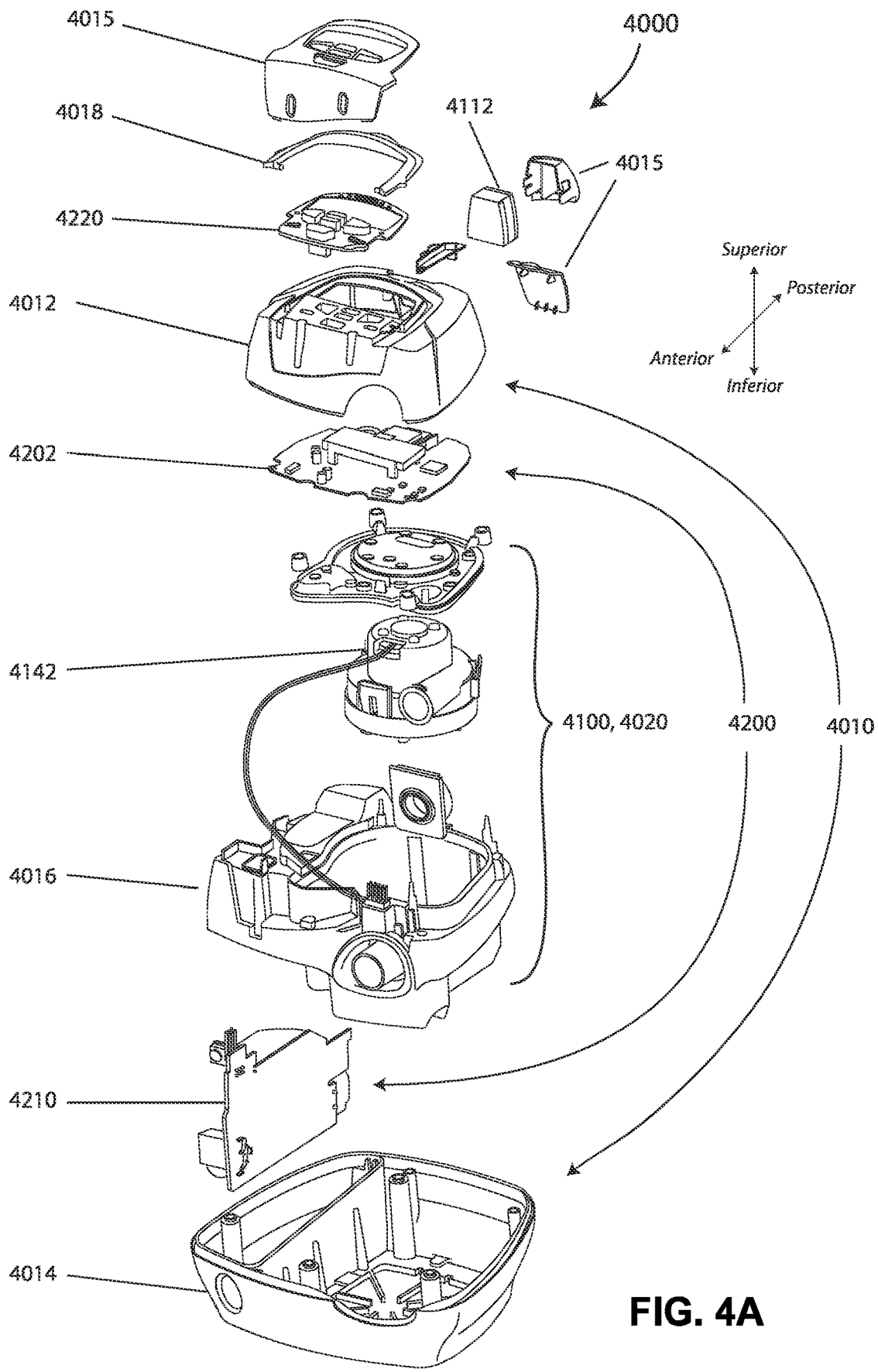
FIG. 4A shows an RPT device in accordance with one form of the present technology.
Figure 4B:
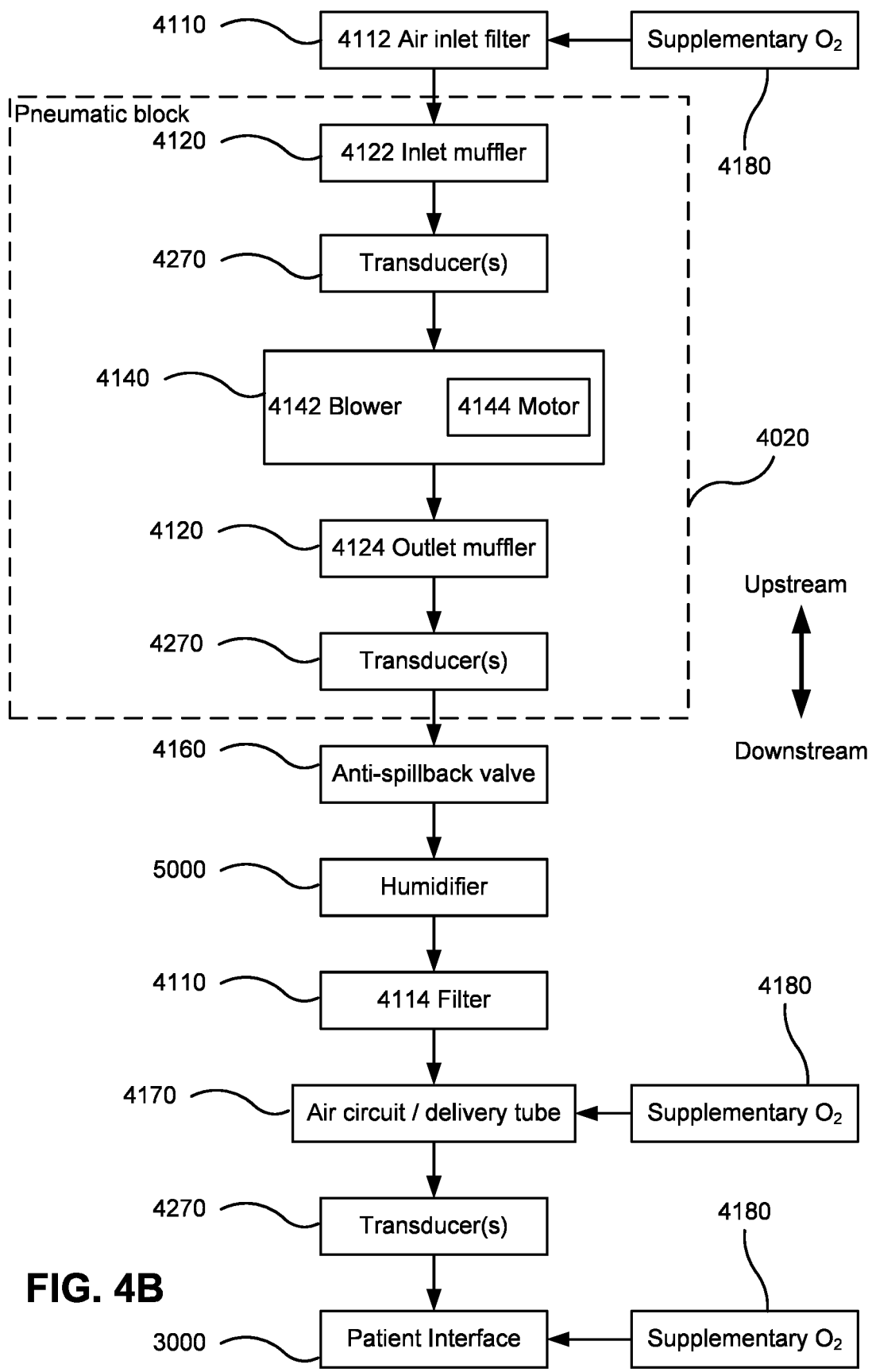
FIG. 4B is a schematic diagram of the pneumatic path of an RPT device in accordance with one form of the present technology. The directions of upstream and downstream are indicated.
Figure 4C:
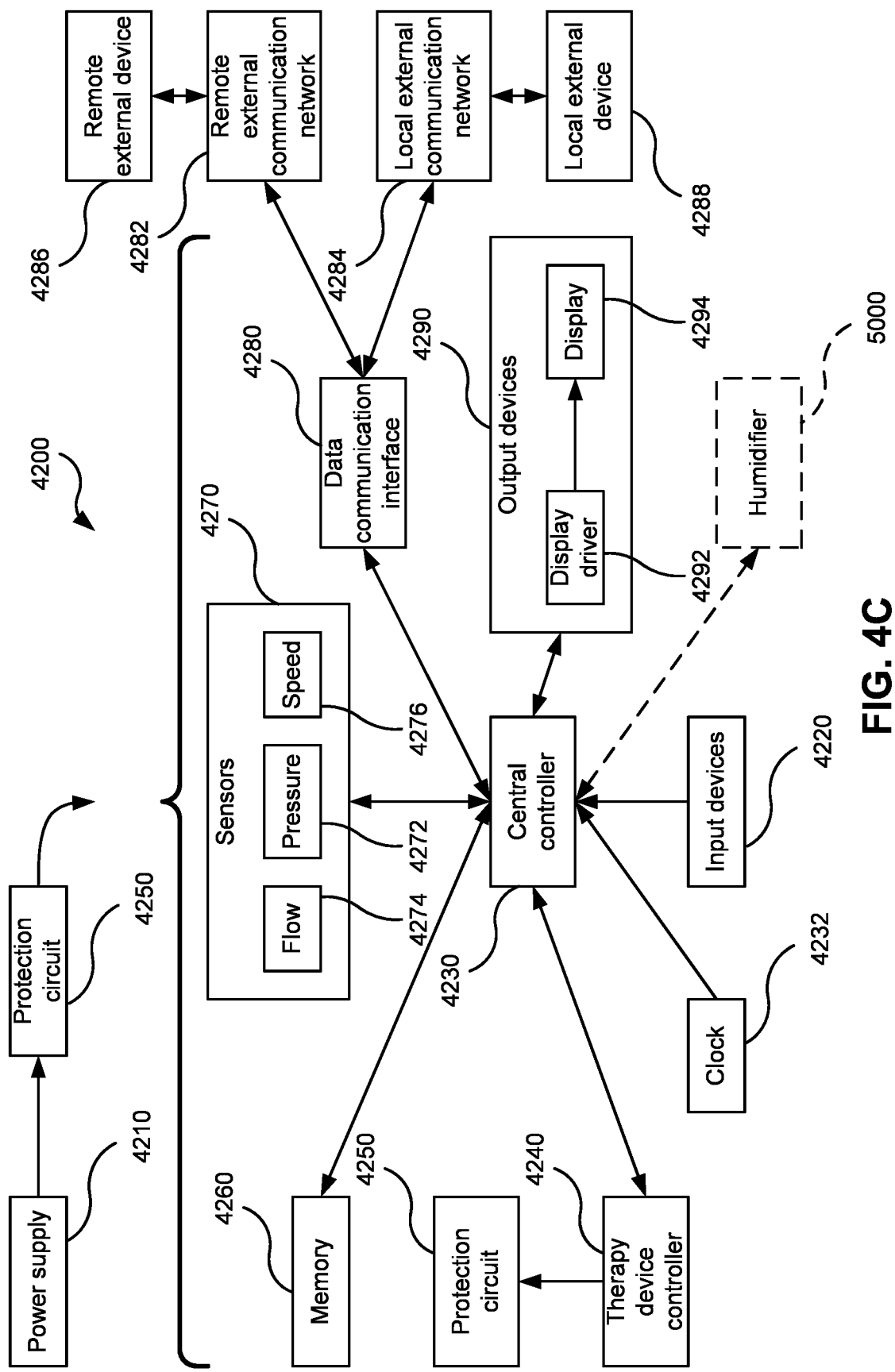
FIG. 4C is a schematic diagram of the electrical components of an RPT device in accordance with one form of the present technology.

FIG. 7A contains a block diagram illustrating one implementation 7000 of an RPT system according to the present technology. The RPT system 7000 comprises an RPT device 4000 configured to provide respiratory pressure therapy to a patient 1000, a data server 7010, and a patient computing device 7050 associated with the patient 1000. The patient computing device 7050 is co-located with the patient 1000 and the RPT device 4000. In the implementation 7000 shown in FIG. 7A, the RPT device 4000, the patient computing device 7050, and the data server 7010 are connected to a wide area network 7090 such as an internet or the Internet. The connections to the wide area network may be wired or wireless. The wide area network may be identified with the remote external communication network 4282 of FIG. 4C, and the data server 7010 may be identified with the remote external device 4286 of FIG. 4C. The patient computing device 7050 may be a personal computer, mobile phone, tablet computer, or other device. The patient computing device 7050 is configured to intermediate between the patient 1000 and the data server 7010 over the wide area network 7090. In one implementation, this intermediation is performed by a software application program 7060 that runs on the patient computing device 7050. The patient program 7060 may be a dedicated application referred to as a "patient app" that interacts with a complementary process hosted by the data server 7010. In another implementation, the patient program 7060 is a web browser that interacts via a secure portal with a web site hosted by the data server 7010. In yet another implementation, the patient program 7060 is an email client.

FIG. 7B contains a block diagram illustrating an alternative implementation 7000B of an RPT system according to the present technology. In the alternative implementation 7000B, the RPT device 4000 communicates with the patient computing device 7050 via a local (wired or wireless) communications protocol such as a local network protocol (e.g., Bluetooth). In the alternative implementation 7000B, the local network may be identified with the local external communication network 4284 of FIG. 4C, and the patient computing device 7050 may be identified with the local external device 4288 of FIG. 4C. In the alternative implementation 7000B, the patient computing device 7050, via the patient program 7060, is configured to intermediate between the patient 1000 and the data server 7010, over the wide area network 7090, and also between the RPT device 4000 and the data server 7010 over the wide area network 7090.

In what follows, statements about the RPT system 7000 may be understood to apply equally to the alternative implementation 7000B, except where explicitly stated otherwise.

The RPT system 7000 may contain other RPT devices (not shown) associated with respective patients who also have respective associated computing devices. All the patients in the RPT system 7000 are managed by the data server 7010.

The RPT device 4000 is configured to store in the memory 4260 therapy data from each RPT session delivered to the patient 1000. Therapy data for an RPT session comprises the settings of the RPT device 4000 and therapy variable data representing one or more variables of the respiratory pressure therapy throughout the RPT session.

The RPT device settings data may include:
Base treatment pressure $P_0$
Maximum and minimum treatment pressure limits Pmax and Pmin
Amplitude A
Humidity of delivered flow of air
Temperature of delivered flow of air
The therapy variables may include:
Respiratory flow rate Qr
Mask pressure Pm
Leak flow rate Ql
Tidal volume Vt
Measure of ventilation Vent
Breathing rate The RPT device 4000 is configured to transmit the therapy data to the data server 7010. The data server 7010 may receive the therapy data from the RPT device 4000 according to a "pull" model whereby the RPT device 4000 transmits the therapy data in response to a query from the data server 7010. Alternatively, the data server 7010 may receive the therapy data according to a "push" model whereby the RPT device 4000 transmits the therapy data to the data server 7010 as soon as convenient after an RPT session.

Therapy data received from the RPT device 4000 is stored and indexed by the data server 7010 so as to be uniquely associated with the RPT device 4000 and therefore distinguishable from therapy data from any other RPT device(s) participating in the RPT system 7000.

The data server 7010 is configured to calculate usage data for each RPT session from the therapy data received from the RPT device 4000. Usage data variables for a session comprise summary statistics derived by conventional scoring means from the therapy variable data that forms part of the therapy data. Usage data may comprise one or more of the following usage variables:

Usage time, i.e. total duration of the RPT session
Apnea-hypopnea index (AHI) for the session
Average leak flow rate for the session
Average mask pressure for the session
Number of "sub-sessions" within the RPT session, i.e. number of intervals of RPT therapy between "mask-on" and "mask-off" events
Other statistical summaries of the therapy variables, e.g. $95^{th}$ percentile pressure, median pressure, histogram of pressure values Usage variables may comprise multi-session statistics, such as mean, median, and variance of AHI since the start of RPT therapy.

In an alternative implementation, the RPT device 4000 calculates the usage variables from the therapy data stored by the RPT device 4000 at the end of each session. The RPT device 4000 then transmits the usage variables to the data server 7010 according to the "push" or "pull" model described above.

In a further implementation, the memory 4260 in which the RPT device 4000 stores the therapy/usage data for each RPT session is in removable form, such as an SD memory card. The removable memory 4260 may be removed from the RPT device 4000 and inserted into a card reader in communication with the data server 7010. The therapy/usage data is then copied from the removable memory 4260 to the memory of the data server 7010.

In still a further implementation, suitable for the alternative implementation 7000B of the RPT system, the RPT device 4000 is configured to transmit the therapy/usage data to the patient computing device 7050 via a wireless communications protocol such as Bluetooth as described above. The patient computing device 7050 then transmits the therapy/usage data to the data server 7010. The data server 7010 may receive the therapy/usage data from the patient computing device 7050 according to a "pull" model whereby the patient computing device 7050 transmits the therapy/usage data in response to a query from the data server 7010. Alternatively, the data server 7010 may receive the therapy/usage data according to a "push" model whereby the patient computing device 7050 transmits the therapy/usage data to the data server 7010 as soon as it is available after an RPT session.

In some implementations, the data server 7010 may carry out some post-processing of the usage data, such as with one or more processors in communication with or included in the data server 7010. One example of such post-processing is to determine whether the most recent session is a "compliant session". Some compliance rules specify the required RPT device usage over a compliance period, such as 30 days, in terms of a minimum duration of device usage per session, such as four hours, for some minimum number of days, e.g. 21, within the compliance period. A session is deemed compliant if its duration exceeds the minimum duration. The usage data post-processing may determine whether the most recent session is a compliant session by comparing the usage duration with the minimum duration from the compliance rule. The result of such post-processing is compliance data, such as a Boolean compliance variable, that forms part of the usage data. A further example of multi-session usage data is a count of compliant sessions since the start of RPT therapy.

The data server 7010 may also be configured to receive data from the patient computing device 7050. Such may include data entered by the patient 1000 to the patient program 7060, or therapy/usage data in the alternative implementation 7000B described above.

The data server 7010 is also configured to transmit electronic messages to the patient computing device 7050. The messages may be in the form of emails, SMS messages, automated voice messages, or notifications within the patient program 7060.

The RPT device 4000 may be configured such that its therapy mode, or settings for a particular therapy mode, may be altered on receipt of a corresponding command via its wide area or local area network connection. In such an implementation, the data server 7010 may also be configured to send such commands directly to the RPT device 4000 (in the implementation 7000) or indirectly to the RPT device 4000, relayed via the patient computing device 7050 (in the implementation 7000B).

The data server 7010 hosts a process 7020, described in detail below, that is configured to increase or sustain the patient's motivation to continue with therapy. In broad terms, the process 7020 analyses data from the RPT device 4000 and/or the patient computing device 7050 to compute a therapy quality indicator that is indicative of the quality of the most recent therapy session. The process 7020 then communicates the therapy quality indicator to the patient 1000, for example via the patient program 7060 running on the patient computing device 7050.

The patient 1000 perceives the therapy quality indicator as a concise indicator of how their therapy is going. The patient 1000 is thereby motivated to persevere with their therapy. It is known that tracking and measuring performance can be a strong motivator for a person to achieve their goals, and the therapy quality indicator serves as such a performance measure in the context of respiratory pressure therapy.

The therapy quality indicator may also be used as a basis to improve the patient's respiratory pressure therapy, as described below.

8.8.2 System Operation

FIG. 8 is a block diagram illustrating a method 8000 carried out by one or more processors of, or in communication with, the data server 7010 in the RPT system 7000 of FIG. 7A or 7000B of FIG. 7B as part of the process 7020 in one form of the present technology. In one form of the present technology, the method 8000 is carried out upon receipt by the data server 7010 of therapy data or usage data for a complete therapy session.

The method 8000 starts at step 8010, at which the data server 7010 processes the therapy data to generate usage data as described above. Step 8010 is shown dashed because it is optional, only being carried out in implementations in which the data server 7010 does not receive usage data from the RPT device 4000 or the patient computing device 7050.

At the next step 8020, the data server 7010 computes a therapy quality indicator from the usage data as described in detail below.

At step 8030, the data server 7010 transmits the therapy quality indicator to the patient computing device 7050 according to one or more of the following implementations:

In an email (when the patient program 7060 is an email client)

In an SMS message

In a "notification" in the patient program 7060 (when the patient program 7060 is a "patient app")

In a page of a web site (when the patient program 7060 is a web browser).

The email, patient app, and web site implementations of step 8030 may contain more information than just the therapy quality indicator. These implementations are described in more detail below.

In some implementations of the process 7020, the method 8000 also includes steps 8040 and 8050 (shown dashed in FIG. 8). At step 8040, the data server 7010 applies one or more rules to the therapy quality indicator computed at step 8020 and, optionally, one or more previously computed values of the therapy quality indicator. Based on the rule output, the data server 7010 at step 8050 may take, or prompt the patient 1000 to take, an action to improve the patient's therapy for subsequent sessions. More details on the rules and actions is given below.

The action taken by the data server 7010 at step 8050 may be altering a setting of the RPT device 4000, or changing the RPT device therapy mode to a different therapy mode.

To prompt the patient 1000 to take an action at step 8050, the data server 7010 may send a message to the patient 1000 via the patient computing device 7050 according to one or more of the following implementations:

In an email

In an SMS message

In a "notification" in the patient program 7060 (when the patient program 7060 is a "patient app")

In a page of a web site (when the patient program 7060 is a web browser).

The content of such a message may be, for example, to adjust the fitting of the patient interface 3000 or change to a different type of patient interface, e.g. from a nasal mask to a full-face mask.

In a further alternative implementation, the method 8000 is carried out upon receipt by the data server 7010 of therapy data or usage data for an interval of duration less than a complete therapy session, for example two hours. In such an implementation, the improvement action (step 8050) may take place within the same session as the usage data from which the therapy quality indicator was computed. The respiratory pressure therapy system 7000 or 7000B therefore takes on a more "real-time" character according to this alternative implementation.

8.8.2.1 Computation of Therapy Quality Indicator

In one implementation of step 8020, the data server 7010 computes the therapy quality indicator as a combination of a plurality of contributions, such as four, each of which corresponds to a different usage variable. The plurality of contributions, each of which may be computed as a points value, correspond to any two or more of usage time, leak, AHI, and session fragmentation. In one version, all four contributions are summed to compute the therapy quality indicator.

Usage Time:

If usage time exceeds a maximum usage time threshold, the usage time contribution is a maximum usage time contribution.

If usage time is less than a minimum usage time threshold, the usage time contribution is a minimum usage time contribution.

If usage time is between the minimum usage time threshold and the maximum usage time threshold, the usage time contribution is proportional to the difference between the usage time and the minimum usage time threshold, such that the usage time contribution is the maximum usage time contribution when the usage time is equal to the maximum usage time threshold.

Leak:

If average leak flow rate exceeds a maximum leak threshold, the leak contribution is a minimum leak contribution.

If average leak flow rate is less than a minimum leak threshold, the leak contribution is a maximum leak contribution.

If average leak flow rate is between the minimum leak threshold and the maximum leak threshold, the leak contribution is proportional to the difference between the maximum leak threshold and the average leak flow rate, such that the leak contribution is the maximum leak contribution when the average leak flow rate is equal to the minimum leak threshold.

AHI Contribution:

If AHI exceeds a maximum AHI threshold, the AHI contribution is a minimum AHI contribution.

If AHI is less than a minimum AHI threshold, the AHI contribution is a maximum AHI contribution.

If AHI is between the minimum AHI threshold and the maximum AHI threshold, the AHI contribution is proportional to the (negative) difference between the AHI and the maximum AHI threshold, such that the AHI contribution is the maximum AHI contribution when the AHI is equal to the minimum AHI threshold.

Fragmentation:

If the number of sub-sessions exceeds a maximum fragmentation threshold, the fragmentation contribution is zero.

If number of sub-sessions is less than or equal to a minimum fragmentation threshold, the fragmentation contribution is a maximum fragmentation contribution.

If number of sub-sessions is between the minimum fragmentation threshold and the maximum fragmentation threshold, the fragmentation contribution is proportional to the difference between the maximum fragmentation threshold and the number of sub-sessions, such that the fragmentation contribution is the maximum fragmentation contribution when the number of sub-sessions is equal to the minimum fragmentation threshold.

The relative values of the maximum usage time contribution, maximum leak contribution, maximum AHI contribution, and maximum fragmentation contribution indicate the relative "weightings" of each usage variable in the therapy quality indicator computation. In one implementation, the usage time is the most highly weighted usage variable, and the average leak flow rate, the AHI, and the fragmentation are equally, relatively lowly, weighted.

The sum of the maximum usage time contribution, maximum leak contribution, maximum AHI contribution, and maximum fragmentation contribution may be a desired target number of points (e.g., 100 points) to ensure that the therapy quality indicator is on a scale (e.g., 100-point scale) for ease of comprehension by the patient 1000.

In one implementation, the parameters for each usage variable are as follows:
minimum usage time threshold: 10 minutes
maximum usage time threshold: $75^{th}$-percentile usage time of patients in the same age cohort as the patient 1000
maximum usage time contribution: 70 points
minimum usage time contribution: 0 points
minimum leak threshold: 10 L/min for patient interface 3000 being a full-face mask, 5 L/min for patient interface 3000 being a nasal mask or nasal pillows
maximum leak threshold: 30 L/min
maximum leak contribution: 10 points
minimum leak contribution: 0 points
minimum AHI threshold: 5 events/hour
maximum AHI threshold: 20 events/hour.
maximum AHI contribution: 10 points
minimum leak contribution: 0 points
minimum fragmentation threshold: 1 sub-session
maximum fragmentation threshold: 5 sub-sessions
maximum fragmentation contribution: 10 points
minimum fragmentation contribution: 0 points The use of other values for the parameters may be used in other implementations of step 8020.

In a variant of the above implementation of step 8020, the leak, AHI, and fragmentation contributions are each reduced in proportion to the ratio of the usage time contribution to the maximum usage time contribution. This variant reduces the relative over-scoring of the therapy quality indicator when usage time is low, such that when usage time is low, the therapy quality indicator is low, even when the other usage variables are good (low leak, AHI, and fragmentation). Other ways of "discounting" the therapy quality indicator as the usage time decreases toward the minimum usage time threshold may also be implemented.

In another variant of the above implementation of step 8020, a bonus or a penalty is applied to the therapy quality indicator based on the usage time in relation to the recent history of usage time. This variant provides personalisation of the therapy quality indicator to an individual patient. In one implementation, the bonus/penalty is computed as proportional to the difference between the usage time and the average of the last seven usage times. The bonus/penalty may be limited to a maximum number of points, and the therapy quality indicator may be limited to the range of 0 to the desired target number of points (e.g., 100 points) after application of the bonus/penalty.

8.8.2.2 Display of Therapy Quality Indicator

The therapy quality indicator, with or without related contributions data, may then be presented to the patient. For example, in the email, web site, and "patient app" implementations of the transmission step 8030, the data server 7010 may transmit more data than the therapy quality indicator alone. FIG. 9 is an example image 9000 illustrating an example therapy quality indicator 9010 and other information that may be transmitted to the patient computing device 7050 by the data server 7010 in an implementation of step 8030 in which the patient program 7060 is a browser. In an implementation in which the patient program 7060 is a web browser, the image 9000 could be a web page. In an implementation in which the patient program 7060 is a "patient app", the image 9000 could be a screenshot of a "patient app". In an implementation in which the patient program 7060 is an email client, the image 9000 could be an image in the body of an email.

In the image 9000, which may form part of a graphic user interface, the therapy quality indicator 9010 (with a value of 63) is displayed within an annular area 9020 beneath the current date 9030. The fraction of the annular area 9020 that is filled, such as with a visual or other color change proportionally about a portion of the circumference of the annular area (in this case 63%) is indicative of the therapy quality indicator. The desired target number of points is also displayed, in this case one hundred points, such as beneath the indicator 9010.

The individual usage variable contributions to the therapy quality indicator may also be transmitted by the data server 7010 and displayed in an area 9040 of the image 9000. The value of each usage variable (e.g. a usage time of 3 hours 31 minutes, at 9042) is displayed in the area 9040. Close to that value, the points contributed to the therapy quality indicator by that usage variable are displayed as a fraction of the maximum point contribution of that usage variable (e.g. 35/70 for usage time, at 9045). Alongside these figure displays are icons (e.g. a clock face 9047) representing the respective usage variables (e.g. usage time for the icon 9047). An optional progress-type line indicator, such as beneath each point contribution, may also be displayed to visually depict the portion of the total points achieved relative to total points achievable for each point contribution. A second instance 9050 of the therapy quality indicator is also displayed within the area 9040 beneath the individual usage variable point contributions of which it is the sum. A progress-type line indicator may also be provided for the sum to visually depict the portion of the total points achieved in relation to the total points achievable (i.e., the desired target number of points).

The patient 1000, by receiving a therapy quality indicator after each therapy session, is thus motivated to persevere, and to target compliance improvement, with their respiratory pressure therapy. The display of the different usage variable contributions to the therapy quality indicator may serve to inform the patient 1000 about any problems with their therapy, and hence to help them identify areas for improvement.

The patient 1000 may also elect to view the recent history of their various usage variables. FIG. 10 is an example image 10000 of a web page, screen shot, or email body that may be transmitted to the patient computing device 7050 by the data server 7010 in various implementations of step 8030. In the image 10000, which may form a part of a graphic user interface, the point contribution 10010 of a chosen usage variable (in the image 10000, this is usage time, with a point contribution of 61) is displayed within an annular area 10020 beneath the date 10030 corresponding to the usage time. The numeric value 10015 of the usage variable (in the image 10000, 5 hours and 45 minutes of usage time) is also displayed below the annular area 10020. Optionally, as illustrated in FIG. 10, beneath the usage variable value 10015, a progress-type line visually depicts the portion of the points achieved relative to the total achievable points for the particularly selected point contribution (i.e., usage time in the illustrated example of FIG. 10.) Moreover, by activating the user interface controls (e.g., "arrow" controls such as forward 10036 and back 10033) the patient is able to move the displayed point contribution backwards and forwards through history, one session at a time.

Beneath the annular area 10020 is a graph 10040 illustrating the history of the point contributions of the chosen usage variable (in the image 10000, this is usage time) over a recent period (in the image 10000, the period is 14 days). In some implementations, the patient is able to move the graph 10040 through the history of the usage variable all the way back to the start of therapy by "swiping" left and right on the graph 10040 when presented on a touch screen type display as a graphical user interface on the display.

By means of the image 10000, the patient is able to get a sense of the recent trend of any usage variable.

The patient 1000 may also elect to view the detail of a therapy variable for the most recent therapy session. FIG. 11 is an example image 11000 of a web page, screen shot, or email body that may be transmitted to the patient computing device 7050 by the data server 7010 in various implementations of step 8030. The image 11000 contains a time trace 11020 of "mask seal" for the therapy session, a variable that is high when leak flow rate Ql is low and vice versa. The image 11000 also contains a time trace 11010 containing dots corresponding to when SDB events (apneas and hypopneas) were detected during the therapy session.

While the aforementioned a therapy quality indicator and related contributions data may be generated by the data server 7010 and displayed via the patient computing device 7050, in some versions, in addition thereto and/or alternatively, the generation and/or display may be effected in or with a processor or controller of an RPT device 4000. Thus, in some cases one or more processors of the RPT device may be configured to calculate and display the therapy quality indicator and/or related contributions data on a display or graphic user interface of the RPT device 4000. Similarly, in some cases one or more processors of the RPT device 4000 may be configured to display the therapy quality indicator and/or related contributions data received from the data server 7010 on a display or graphic user interface of the RPT device 4000.

8.8.2.3 Improvement of Therapy

As mentioned above, in optional steps 8040 and 8050, the data server 7010 applies one or more rules to the therapy quality indicator computed at step 8020 and, optionally, one or more previously computed values of the therapy quality indicator, and takes, or prompts the patient 1000 to take, an action to improve the patient's therapy.

In one example of a rule/action pair, if the therapy quality indicators indicate persistent high leak flow rates over recent therapy sessions, the data server 7010 may prompt the patient 1000 to adjust the fitting of their patient interface 3000, or to change the type of patient interface 3000.

In another example of a rule/action pair, if the therapy quality indicators indicate declining usage times over recent therapy sessions, and the season is conducive to nasal congestion (e.g. winter), the data server 7010 may increase the humidity of the delivered flow of air to reduce the amount of nasal congestion.

In another example of a rule/action pair, if the therapy quality indicators have been steadily high over recent therapy sessions, the data server 7010 may send a message to the patient that they can have a reward, such as a "night off" from their therapy.

In an alternative implementation of the method 8000, the data server 7010 after step 8040 does not immediately take or prompt an action, but issues a query to the patient 1000. The data server 7010 may issue a query to the patient 1000 via the patient computing device 7050 and/or RPT device 4000 according to one or more of the following implementations:

In an email
In an SMS message
In a "notification" in the patient program 7060 (when the patient program 7060 is a "patient app")
In a page of a web site (when the patient program 7060 is a web browser).

The data server then takes the response to the query (which is framed so as to elicit a yes/no response) into account before taking or prompting the action at step 8050 as described above.

In one example of such a rule/query/action sequence, if the therapy quality indicators indicate persistent high leak flow rates over recent therapy sessions, the data server 7010 may issue the query "Do you have a dry mouth on waking?" If the received answer to the query is yes, the data server 7010 may prompt the patient 1000 to use a full-face mask, or a chin strap with a nasal mask, to reduce mouth leak.

In another example of such a rule/query/action sequence, if the therapy quality indicators indicate declining usage times or increasing on/off events over recent therapy sessions, the data server 7010 may issue the query "Are you having trouble getting to sleep?" If the received answer to the query is yes, the data server 7010 may change the therapy mode to deliver paced breathing therapy for a first portion of the therapy session so as to relax and settle the patient, before switching to the patient's regular therapy mode.

In yet another example of a rule/query/action sequence, if the therapy quality indicators indicate declining usage times over recent therapy sessions, and the season is conducive to nasal congestion (e.g. winter), the data server 7010 may issue the query "Are you experiencing nasal congestion?" If the received answer to the query is yes, the data server 7010 may increase the humidity of the delivered flow of air to reduce the amount of nasal congestion.

In still another example of such a rule/query/action sequence suitable for patients whose SDB is comorbid with heart failure, if the therapy quality indicators indicate declining usage times or increasing on/off events or increasing AHI over recent therapy sessions, the data server 7010 may issue the query "Are you experiencing shortness of breath?" If the received answer to the query is yes, the data server 7010 may issue an alert to the patient that the patient's heart failure condition is worsening and that they should visit their doctor.

8.9 Glossary

For the purposes of the present technology disclosure, in certain forms of the present technology, one or more of the following definitions may apply. In other forms of the present technology, alternative definitions may apply.

8.9.1 General

Air: In certain forms of the present technology, air may be taken to mean atmospheric air, and in other forms of the present technology air may be taken to mean some other combination of breathable gases, e.g. atmospheric air enriched with oxygen.

Respiratory Pressure Therapy (RPT): The application of a supply of air to an entrance to the airways at a treatment pressure that is continuously positive with respect to atmosphere.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

8.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea is taken to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

8.9.3 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate is given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Leak: An unintended flow of air. In one example, leak may occur as the result of an incomplete seal between a mask and a patient's face. In another example leak may occur in a swivel elbow to the ambient.

8.10 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

8.11 Reference Signs List patient 1000
bed partner 1100
patient interface 3000
seal-forming structure 3100
plenum chamber 3200
structure 3300
vent 3400
connection port 3600
forehead support 3700
RPT device 4000
external housing 4010
upper portion 4012
portion 4014
panel 4015
chassis 4016
handle 4018
pneumatic block 4020
pneumatic components 4100
inlet air filter 4112
inlet muffler 4122
outlet muffler 4124
pressure generator 4140
blower 4142
air circuit 4170
air circuit 4171
electrical components 4200
Printed Circuit Board Assembly 4202
electrical power supply 4210
input devices 4220 central controller 4230
therapy device controller 4240
protection circuits 4250
removable memory 4260
transducers 4270
pressure sensor 4272
flow rate sensor 4274
data communication interface 4280
remote external communication network 4282
local external communication network 4284
remote external device 4286
local external device 4288
output devices 4290
humidifier 5000
humidifier inlet 5002
humidifier outlet 5004
humidifier base 5006
reservoir 5110
conductive portion 5120
humidifier reservoir dock 5130
locking lever 5135
water level indicator 5150
humidifier transducers 5210
pressure transducers 5212
flow rate transducers 5214
temperature transducers 5216
humidity sensors 5218
heating element 5240
humidifier controller 5250
central humidifier controller 5251
heating element controller 5252
air circuit controller 5254
RPT system 7000
implementation 7000B
data server 7010
process 7020
patient computing device 7050
patient program 7060
wide area network 7090
method 8000
step 8010
step 8020
step 8030
step 8040
step 8050
image 9000
therapy quality indicator 9010
annular area 9020
current date 9030
area 9040
value 9042
fraction 9045
clock face 9047
second instance 9050
image 10000
value 10010
annular area 10020
date 10030
arrow 10033
arrow 10036
graph 10040
image 11000
time trace 11010
time trace 11020

The invention claimed is:

1. A respiratory pressure therapy system comprising:
one or more processors configured to access data associated with usage of a respiratory pressure therapy device that delivers a respiratory pressure therapy to a patient in multiple sessions, the one or more processors being further configured to:
determine a therapy quality indicator of a session of the multiple sessions from usage data relating to the session, the therapy quality indicator being a number derived from adding a plurality of contributions, each of which corresponds to a different usage variable for the session in the usage data, wherein the usage variables comprise at least one of usage time of the session, apnea-hypopnea index for the session, average leak flow rate for the session, and number of sub-sessions within the session, and wherein (a) at least one of the plurality of contributions is set to a first maximum contribution based on a corresponding usage variable exceeding a maximum threshold for that usage variable, or (b) at least one of the plurality of contributions is set to a second maximum contribution based on a corresponding usage variable being less than a minimum threshold for that usage variable; and
based on the therapy quality indicator, (a) alter a setting of the respiratory pressure therapy device, (b) change a therapy mode of the respiratory pressure therapy device, or (c) send a message to a computing device associated with the patient, wherein the message prompts the patient to adjust a component of the respiratory pressure therapy system that is associated with delivering the respiratory pressure therapy.

2. The respiratory pressure therapy system of claim 1, wherein the one or more processors are further configured to receive the usage data from the respiratory pressure therapy device.

3. The respiratory pressure therapy system of claim 1, wherein the one or more processors are further configured to receive the usage data from the computing device associated with the patient.

4. The respiratory pressure therapy system of claim 3 further comprising the computing device.

5. The respiratory pressure therapy system of claim 1, wherein the usage variables comprise two or more of a group consisting of:
usage time of the session;
apnea-hypopnea index for the session;
average leak flow rate for the session; and
number of sub-sessions within the session.

6. The respiratory pressure therapy system of claim 5, wherein the usage variables further comprise one or more of a group consisting of:
average mask pressure for the session; and
whether the session is a compliant session according to a compliance rule.

7. The respiratory pressure therapy system of claim 5, wherein the therapy quality indicator is a sum of the plurality of contributions.

8. The respiratory pressure therapy system of claim 1, wherein at least one of the plurality of contributions is set to the first maximum contribution, and the corresponding usage variable exceeds the threshold for that usage variable.

9. The respiratory pressure therapy system of claim 1, wherein at least one of the plurality of contributions is a minimum contribution, and the corresponding usage variable is less than a threshold for that usage variable.

10. The respiratory pressure therapy system of claim 1, wherein at least one of the plurality of contributions is a minimum contribution, and the corresponding usage variable exceeds a threshold for that usage variable.

11. The respiratory pressure therapy system of claim 1, wherein at least one of the plurality of contributions is set to the second maximum contribution, and the corresponding usage variable is less than the threshold for that usage variable.

12. The respiratory pressure therapy system of claim 1, wherein the plurality of contributions comprises a first contribution and a second contribution, and wherein the first contribution is reduced in proportion to a ratio of the second contribution to the maximum contribution.

13. The respiratory pressure therapy system of claim 1, wherein the one or more processors are further configured to apply a bonus or penalty to at least one of the plurality of contributions based on a value of the corresponding usage variable in relation to a recent history of that usage variable.

14. The respiratory pressure therapy system of claim 1, wherein the one or more processors are configured to alter a setting of the respiratory pressure therapy device based on the therapy quality indicator.

15. The respiratory pressure therapy system of claim 1, wherein the one or more processors are configured to change a therapy mode of the respiratory pressure therapy device based on the therapy quality indicator.

16. The system of claim 1, wherein the message to a computing device is configured to prompt the patient to adjust fitting of a patient interface through which the respiratory pressure therapy is being delivered based on the therapy quality indicator.

17. The respiratory pressure therapy system of claim 1 further comprising the respiratory pressure therapy device.

18. The respiratory pressure therapy system of claim 1, wherein each contribution of the plurality of contributions indicates a relative weighting of its corresponding usage variable in computing the therapy quality indicator.

19. A method for providing respiratory pressure therapy compliance information, the method comprising:
   computing, with one or more processors, a therapy quality indicator of a session of respiratory pressure therapy from usage data relating to the session, wherein the therapy quality indicator is a number derived from a plurality of contributions, each of which corresponds to a different usage variable for the session in the usage data, wherein the usage variables comprise at least one of usage time of the session, apnea-hypopnea index for the session, average leak flow rate for the session, and number of sub-sessions within the session, and wherein (a) at least one of the plurality of contributions is set to a first maximum contribution based on a corresponding usage variable exceeding a maximum threshold for that usage variable, or (b) at least one of the plurality of contributions is set to a second maximum contribution based on a corresponding usage variable being less than a minimum threshold for that usage variable; and
   based on the therapy quality indicator, changing a therapy mode of a respiratory pressure therapy device, wherein the usage variables comprise two or more of the following: i) apnea-hypopnea index for the session, ii) average leak flow rate for the session, iii) number of sub-sessions within the session, iv) average mask pressure for the session, and v) whether the session is a compliant session according to a compliance rule.

20. The method of claim 19, wherein each contribution of the plurality of contributions indicates a relative weighting of its corresponding usage variable in computing the therapy quality indicator.

21. The method of claim 20, wherein the therapy mode is altered from i) a paced breathing therapy mode to ii) a regular therapy mode.

22. A respiratory pressure therapy system comprising:
   one or more processors configured to access data associated with usage of a respiratory pressure therapy device that delivers a respiratory pressure therapy to a patient in multiple sessions, the one or more processors being further configured to:
   determine a therapy quality indicator of a session of the multiple sessions from usage data relating to the session, the therapy quality indicator being a number derived from adding a plurality of contributions, each of which corresponds to a different usage variable for the session in the usage data, wherein the usage variables comprise at least one of usage time of the session, apnea-hypopnea index for the session, average leak flow rate for the session, and number of sub-sessions within the session, and wherein (a) at least one of the plurality of contributions is set to a first maximum contribution based on a corresponding usage variable exceeding a maximum threshold for that usage variable, or (b) at least one of the plurality of contributions is set to a second maximum contribution based on a corresponding usage variable being less than a minimum threshold for that usage variable; and
   based on the therapy quality indicator, send a message to a computing device associated with the patient, wherein a content of the message identifies a component of the respiratory pressure therapy system that is associated with delivering the respiratory pressure therapy and informs the patient to adjust the component of the respiratory pressure therapy system.

23. The respiratory pressure therapy system according to claim 21, wherein the adjusted component is a patient interface through which the respiratory therapy is delivered.

* * * * *